(12) United States Patent
Beach et al.

(10) Patent No.: US 6,322,975 B1
(45) Date of Patent: Nov. 27, 2001

(54) ASSAYS AND REAGENTS FOR IDENTIFYING MODULATORS OF CDC25-MEDIATED MITOTIC ACTIVATION

(76) Inventors: David H. Beach, 19 Woodland Dr., Huntington Bay, NY (US) 11743; Konstantin Galaktionov, One Bungtown Rd., Cold Spring Harbor, NY (US) 11724

( * ) Notice: Subject to any disclaimer, the term of this patent is extended or adjusted under 35 U.S.C. 154(b) by 0 days.

(21) Appl. No.: 09/232,063

(22) Filed: Jan. 15, 1999

Related U.S. Application Data

(63) Continuation of application No. 08/636,597, filed on Apr. 23, 1996, now Pat. No. 5,861,249.

(51) Int. Cl.[7] .............................. C12Q 1/68; G01N 33/53; C07H 21/02; C07H 21/04

(52) U.S. Cl. .............................. 435/6; 435/7.31; 435/7.32; 435/254.11; 435/29; 435/21; 435/254.2; 536/23.1; 536/24.1

(58) Field of Search .............................. 435/6, 7.31, 7.32, 435/254.11, 29, 21, 254.2; 536/23.1, 24.1

(56) References Cited

U.S. PATENT DOCUMENTS

| | | | |
|---|---|---|---|
| 5,426,177 | * 6/1995 | Davis et al. | 530/395 |
| 5,443,962 | * 8/1995 | Draetta et al. | 435/29 |
| 5,843,654 | * 12/1998 | Heisler et al. | 435/6 |
| 5,955,263 | * 9/1999 | Vogelstein et al. | 435/6 |

* cited by examiner

Primary Examiner—Jeffrey Fredman
Assistant Examiner—Arun Kr. Chakrabarti

(57) ABSTRACT

The present invention makes available assays and reagents for identifying agents which can be used to modulate at least one proliferation, differentiation and cell death by apoptosis.

8 Claims, 6 Drawing Sheets

GAGTCGTGTTTGTGTTTGACCCGGTGGGCGCCGAGGCCGGTGTCGGCGGG
GCGGGGCGGTCGCGGAGGCAGAGAGGAGCGGGAGCTCTGCGAGGCGCGCCG
CCATGGAACTAGGCCCCGGAGCCCCGCCGCCTGCTCTTCGCCTGCAGCCCCC
CTCCCGCGTCGCAGCCCGTCGTGAAGGCGCTATTTGGCGCTTCAGCGCCGGGGACTGTCG
CCTGTCACCAACCTGACCGTCACTATGGACCAGCTGCAGGGTCTTGGCAGGTAAGGAGAGAC
CGCGGGCGGTGCTCCGGCCCTCGGTGTCGGCCTTCGGCGAGAGTTCAGGCCAGGAAAC
GGACCGGAGAAGGGCGAGACCCGTCCGTTCCGCTCGGGGAGAGGCCGGGCTAGG
GCCTGCCATGTGCACCCCCGCCCCGGGAATGTTGGCCCGGACCCCAGGCCCCCC
CAGGGGAAGAGAGGTGGAGATCCTTGGGCCTAAGCCCGACCCAGCCCCCC

F2

GAGTCGGGGATGAAAGTTGAACAGGACACTTTCTGCTTTTCAGAAGTTGGGAAACGCACAAGA
CATGTGCTTAGCAAACGGATGCCAGAGATTGAAGGGAAAGTAGCTCTTCCGCGGGAAA
CACCGTGGGATGCATTTTTTGCTATCAGGAAAAGCCCAGGAAGCTTTCTGAAAGTTGGGTAA
AAAGACCTGGCTTAGGAAAGCAGGAGTGGACATCAGGAATGTGCACAGGGCGAGGGACT
GAGATGATTTACATAAACGCCAGGAAAGGAAATGCCATGGTCCTTTGTTGAGAAGAACAA
AGATCACAGCAAACGAAGATCCTGAGGATGGTTTAGAAAAGGGTGAAAGTGAGTGCCTAGAA
GAGCCCTGATTTTCCCGGGGGTAGATT

FIG. 3

|       | -8       |         | +18          |
|-------|----------|---------|--------------|
| MBA1  | GGGCCTGC | CATGTG | CACCCCGCCCGGG |
| MBA2  | GCACAAGA | CATGTG | CTTAGCAAACGGG |
| MBA3  | ACTACAGA | CACGTG | CCACCACACCCAA |
|       |          |         |              |
| ODC1  | TGTGCGGC | CACGTG | TCGCGAGGCCCCG |
| ODC2  | GCAGGGGA | CACGTG | GTCGCCGAGCGNN |
| PT    | GCAACGAG | CACGTG | GCCTGGGGCGCCA |
|       |          |         |              |
| Cons. | C̲ C̲ G   | CAC̲GTG  | C̲C̲   A   CC̲ G̲ |
|       | G G      | T       | GT   C   G A |

ASSAYS AND REAGENTS FOR IDENTIFYING MODULATORS OF CDC25-MEDIATED MITOTIC ACTIVATION

This application is a continuation of Ser. No. 08/636,597, Apr. 23, 1996, now U.S. Pat. No. 5,861,249.

BACKGROUND OF THE INVENTION

The progression of a proliferating eukaryotic cell through the cell-cycle checkpoints is controlled by an array of regulatory proteins that guarantee that mitosis occurs at the appropriate time. Protein phosphorylation is the most common post-translational modification that regulates processes inside the cells, and a large number of cell cycle transitions are regulated by, in addition to protein-protein interactions, the phosphorylation states of various proteins. In particular, the execution of various stages of the cell-cycle is generally believed to be under the control of a large number of mutually antagonistic kinases and phosphatases. A paradigm for these controls are the cyclin dependent kinases (CDKs), whose activity is required for the triggering of mitosis in eukaryotic cells (for reviews, see Hunt (1989) *Curr. Opin. Cell Biol.* 1:268–274; Lewin (1990) *Cell* 61:743–752; and Nurse (1990) *Nature* 344:503–508). During cell-cycle progression, CDKs appear to trigger a cascade of downstream mitotic phenomena such as metaphase alignment of chromosomes, segregation of sister chromatids in anaphase, and cleavage furrow formation.

The CDKs are subject to multiple levels of control. These proteins are positively regulated by association with cyclins (Evans et al. (1983) *Cell* 33:389–396; Swenson et al. (1986) *Cell* 47:861–870; Xiong et al. (1991) *Cell* 65:691–699; Matsushime et al. (1991) *Cell* 66:701–713; Koff et al. (1991) *Cell* 66:1217–1228; Lew et al. (1991) *Cell* 66:1197–1206) and activating phosphorylation by the cdk activating kinase (CAK) (Solomon et al. (1992) *Mol Biol. Cell* 3:13–27). Negative regulation of the cyclin/cdk(s) is achieved independently by at least two different mechanisms: binding of the inhibitory subunits (p21, p16, p15, p27 and p18) (c.f., Xiong et al. (1993) *Nature* 366,701–704; Harper et al. (1993) *Cell* 75:805–816; El-Deiry et al. (1993) *Cell* 75:817–825; Gu et al. (1993) *Nature* 366:707–710; Serrano et al. (1993) *Nature* 366:704–707; Hannon et al. (1994) *Nature* 371:257–261; Polyak et al. (1994) *Cell* 78:59–66; Toyoshima et al. (1994) *Cell* 78:67–74; Guan et al. (1994) *Genes and Dev.* 8:2939–2950) and by phosphorylation of conservative threonine and tyrosine residues, usually at positions 14 and 15 in cdk(s) (Gould et al. (1989) *Nature* 342:81–86; Krek et al. (1991) *EMBO J.* 10:3331–3341; Gu et al. (1992) *EMBO J.* 11:3995–4005; and Meyerson et al. (1992) *EMBO J.* 11:2909–2917).

The phosphorylation of CDC2 on Tyr-15 and Thr-14, two residues located in the putative ATP binding site of the kinase, negatively regulates kinase activity. This inhibitory phosphorylation of CDC2 is mediated at least in part by the wee1 and mik1 tyrosine kinases (Russel et al. (1987) *Cell* 49:559–567; Lundgren et al. (1991) *Cell* 64:1111–1122; Featherstone et al. (1991) *Nature* 349:808–811; and Parker et al. (1992) PNAS 89:2917–2921). These kinases act as mitotic inhibitors, over-expression of which causes cells to arrest in the G2 phase of the cell-cycle. By contrast, loss of function of wee1 causes a modest advancement of mitosis, whereas loss of both wee1 and mik1 function causes grossly premature mitosis, uncoupled from all checkpoints that normally restrain cell division (Lundgren et al. (1991) *Cell* 64:1111–1122).

A stimulatory phosphatase, known as cdc25, is responsible for Tyr-15 and Thr-14 dephosphorylation and serves as a rate-limiting mitotic activator. (Dunphy et al. (1991) *Cell* 67:189–196; Lee et al. (1992) *Mol. Biol. Cell.* 3:73–84; Millar et al. (1991) *EMBO J.* 10:4301–4309; and Russell et al. (1986) *Cell* 45:145–153). In humans, there are three known cdc25-related genes which share approximately 40–50% amino-acid identity (Sadhu et al. (1990) PNAS 87:5139–5143; Galaktionov and Beach (1991) *Cell* 67:1181–1194; and Nagata et al. (1991) *New Biol.* 3:959–968). Human cdc25 genes were recently found to function at G1 and/or S-phase of the cell cycle (Jinno et al. (1994) *EMBO J.* 13:1549–1556) in addition to the previously identified $G_2$ or M-phase functions (Galaktionov and Beach, D. ibid.; Millar, et al. (1991) PNAS 88:10500–10504).

The c-myc protooncogene belongs to a family of related genes implicated in the control of normal cell proliferation and the induction of neoplasia. See, for example, Bishop, J. M. (1983) Annu. Rev. Biochem. 52, 301–354; Albrecht et al. (1992) Biochim. Biophys. Acta 1114, 129–146; Alitalo et al. (1987) Biochim. Biophys. Acta 907, 1–32; and Bornkamm, G. W. and Lenoir, G. M. In Advances in Viral Oncology, Vol 7. Klein, G. Ed.,173–206. Raven Press, N.Y. (1987). The first identified member of the family, v-myc, was found as a transforming gene of the MC29 and MHz avian retroviruses. A cellular homolog was later identified and isolated (Vennstrom et al. (1982) J Virol 42, 773–779). C-myc expression is associated with mitogenic activation in many cell types (Spencer et al. (1991) Adv. Cancer. Res. 56, 1–48; and Marcu et al. (1992) Annu. Rev. Biochem. 61, 809–860). Oncogenic activation of the gene in non-virally infected cells results from constitutive over-expression caused often by gene amplification, and has not been generally associated with mutation in the protein coding sequence (Lusher et al. (1990) Genes Dev. 4, 2025–2035; and Penn et al. (1990) Semin. Cancer Biol. 1, 69–80). More recently, c-myc has been implicated in the induction of apoptosis or programmed cell death (Askew et al. (1991) Oncogene 6, 1915–1922; and Evan et al. (1992) Cell 69, 119–128). Myc-induced apoptosis is enhanced by growth factor deprivation and the oncogenic-apoptotic switch is sensitive to the level of mitogenic stimulation.

The c-Myc protein (Myc) contains several structural motifs characteristic of sequence-specific transcription factors (Stone et al. (1987) Mol. Cell. Biol. 7, 1697–1709; Freytag et al. (1990) Cell Growth Differ. 1, 339–343; and Penn et al. (1990) Mol. Cell. Biol. 10, 4961–4966). The biological activity of Myc depends on the integrity of an N-terminal transactivation domain and a carboxy-terminal basic-helix-loop-helix-leucine zipper (b-HLH-LZ) domain (Kato et al. (1990) Mol. Cell. Biol. 10, 5914–5920; Blackwell et al. (1990) Science 250, 1149–1151; and Blackwood et al. (1991) Science 251, 1211–1217). The latter promotes association with Max, an essential partner, creating a sequence-specific DNA binding complex that recognizes a core hexanucleotide motif (CA(C/T)GTG). Myc alone binds DNA poorly and in vivo exist primarily in association with Max. Both Myc-Max and Max-Max dimers co-exist in equilibrium and bind to the same sequence motif in vitro. However, Myc overexpression activates, whereas Max over-expression represses, a CACGTG-driven reporter gene (Kretzner et al. Nature 359, 426429).

The function of Myc in oncogenesis and the induction of apoptosis is inhibited by mutations that inactivate transcription activation and leucine zipper domains. Complementary Myc and Max mutants, while defective in binding to the wild type partners, restore Myc transforming activity when coexpressed in cells, showing that Myc/Max interaction is essential for the Myc transforming activity (Amati et al. (1993) Cell 72, 233–245). Myc activity in cell cycle progression and apoptosis also requires the presence of both intact transactivation and Max binding domains. Thus, Myc displays the properties of a transcriptional activator which requires dimerization with Max to bind DNA. Following mitogenic stimulation of quiescent fibroblast cells the intracellular level of Myc is induced within 3–5 hours and then decreases to a constant intermediate level, whereas the level of Max is growth factor independent. Thus, the abundance of Myc appears to be the rate limiting determinant of Myc/Max activity (Kretzner et al. Nature 359, 426–429; and Ayer et al. (1993) Cell 72, 211–222.).

Few transcriptional targets of c-myc have been identified (Packham et al. (1995) Biochim. Biophys. Acta 1242: 11–28). One, ornithine decarboxylase (ODC), is an essential enzyme involved in the synthesis of polyamines. ODC displays certain oncogenic properties, suggesting that it might be an important c-myc target. Recently, it has been shown that induction of Myc in growth factor depleted cells causes rapid activation of the cyclin E/cdk2 kinase without alteration in the abundance of cdk2 or cyclin E (Steiner et al. (1995) EMBO J. 14:4814–4826).

SUMMARY OF THE INVENTION

The present invention makes available assays and reagents for identifying agents which can be used to modulate at least one proliferation, differentiation and cell death by apoptosis.

In one aspect of the invention, there is provides an assay for identifying an inhibitor of cdc25-mediated mitotic activation, comprising (i) providing a population of test cells comprising a recombinant cdc25 phosphatase gene, which gene is expressible to levels in the cell which can cause apoptosis; (ii) contacting the test cell population with a candidate agent under conditions wherein the recombinant cdc25 phosphatase gene is expressed; (iii) determining the amount of cell death the test cell population in the presence of the candidate agent; and (iv) comparing the amount of cell death in the presence of the candidate agent to an amount of cell death occurring in the absence of the candidate agent. A statistically significant decrease in the amount of cell death in the presence of the candidate agent is indicative of an inhibitor of cdc25-mediated mitotic activation. In preferred embodiments, the recombinant cdc25 gene is inducibly expressible and the amount of cell death in the presence and the absence of the candidate agent is measured under conditions wherein the recombinant cdc25 gene is expressed. Moreover, it will be generally desirable that the recombinant cdc25 gene encodes a mammalian cdc25 phosphatase, e.g., a human cdc25 phosphatase such as cdc25A, cdc25B and cdc25C.

The cells in which the subject assay is derived are preferable mammalian cells, and even more preferably are human cells. For example, a mammalian cell having at least one functional p53 tumor supressor allele can be used to generate the present assay.

In another aspect, the present invention provides an assay for identifying an agent which modulates cdc25-mediated mitotic activation, comprising (i) providing a population of test cells comprising a recombinant cdc25 phosphatase gene, which gene is expressible to levels in the cell which can cause apoptosis; (ii) contacting the test cell population with a candidate agent under conditions wherein the recombinant cdc25 phosphatase gene is expressed; (iii) determining the amount of a diagnostic protein in the test cell population in the presence of the candidate agent, the level of which diagnostic protein is modulated by cdc25-mediated apoptosis; and (iv) comparing the amount of the diagnostic protein in the presence of the candidate agent to an amount occurring in the absence of the candidate agent. A statistically significant change in the amount of the diagnostic in the presence of the candidate agent is indicative of a modulator of cdc25-mediated mitotic activation. In an exemplary embodiment, the protein which is diagnostic of apoptosis is a p53 tumor supressor protein. Such protein can be measured by, for example, an immunoassay a DNA binding assay, gel electrophoresis, and/or reporter gene transcription.

As above, the recombinant cdc25 gene is preferably expressed from an inducible expression system, and the amount of diagnostic protein in the presence and the absence of the candidate agent is measured under conditions wherein the recombinant cdc25 gene is expressed. Likewise, preferred embodiments will employ mammalian cdc25 phosphatase, especially human cdc25 phosphatases such as cdc25A, cdc25B and cdc25C.

In still another aspect of the invention, an assay for identifying an inhibitor of cdc25-mediated mitotic activation is provided which comprises: (i) providing a cell comprising (a) a recombinant cdc25 phosphatase gene, and (b) a reporter gene under transcriptional control of a p53 responsive element; (ii) contacting the cell with a candidate agent under conditions wherein the recombinant cdc25 gene is expressed; (iii) detecting the level of expression of the reporter gene; and (iv) comparing the measured level of reporter gene expression in the presence of the candidate agent with a level of expression in the absence of the candidate agent. Accordingly, a statistically significant decrease in level of expression of the reporter gene, relative to a level of expression in the absence of the candidate agent, is indicative of cdc25-mediated mitotic activation. Exemplary reporter genes can comprise a transcriptional control element selected from a group consisting of a p53 promoter, and a CYC1 hybrid promoter containing a p53-binding sequence. As illustrated below, the reporter gene can be a recombinant luciferase gene, or other gene product which is readily detected.

The present invention also provides a recombinant cell comprising a recombinant cdc25 phosphatase gene, and a reporter gene under transcriptional control of a p53 responsive element. In preferred embodiments, the recombinant cdc25 gene comprises a transcriptional regulatory sequence providing for inducible expression of a cdc25 phosphatase encoded by the gene, and encodes a mammalian cdc25 phosphatase.

Still another aspect of the present invention relates to a method of identifying an inhibitor of myc-mediated transcriptional activation. In general, such assays comprise: (i) measuring the amount of binding of a myc protein to an isolated nucleic acid which conforms to the consensus binding site CAYGTG, such as represented in the degenerate sequence WGNCAYGTGCNNNNMNNNMCSRR or other fragments of a cdc25 gene, e.g., a cdc25A or cdc25B gene; (ii) measuring the amount of binding of the myc protein to the nucleic acid in the presence of a test substance; and (iii) comparing the amount of binding of the myc protein in the presence of the test substance to the amount of binding of the myc protein in the absence of the test substance. A statistically significant decrease in the amount of binding indicates that the test substance is a potential inhibitor of myc-mediated transcriptional activation.

In an alternate embodiment, the method comprises (i) contacting a transfected cell with a test substance, the transfected cell comprising a myc protein and a recombinant reporter gene construct comprising a reporter gene which encodes an assayable product and a sequence which conforms to the myc consensus binding site CAYGTG, wherein the sequence transcriptionally regulates the reporter gene; and (ii) determining whether the amount of expression of the reporter gene is altered by the test substance.

In each embodiment, the myc consensus binding site preferably is derived from the transcriptional regulatory sequence of a cdc25A gene.

Accordingly, the present invention also provides an (isolated) nucleic acid construct for use in identifying an inhibitor of myc-mediated transcriptional activation. The construct includes a reporter gene which encodes an assayable product; and a myc-responsive transcriptional regulatory sequence which conforms to the myc consensus binding site CAYGTG, which regulatory sequence controls expression of the reporter gene. The construct is preferably selected from the group consisting of a recombinant plasmid, a viral vector and an isolated molecule of nucleic acid.

Another aspect of the present invention provides a recombinant cell comprising an expression vector including a reporter gene which encodes an assayable product and a transcriptional regulatory sequence of a cdc25A gene including a myc-responsive transcriptional regulatory sequence, which regulatory sequence are operably linked to and control expression of the reporter gene.

Still another aspect of the present invention pertains to a method for preventing apoptosis of a cell by contacting the cell with an amount of an agent capable of inhibiting myc-induced upregulation of a cdc25 phosphatase. For instance, the agent can prevent cell death by inhibiting transcriptional activation of a cdc25 phosphatase gene by a myc transcriptional complex, or otherwise inhibiting expression of the cdc25 phosphatase gene. Alternatively, the agent can directly inhibit the phosphatase activity of the cdc25 protein encoded by the cdc25 phosphatase gene, or inhibit its allosteric activation. In yet other embodiments, the agent can alter the stability of the cdc25 protein, or its interaction with other cellular factors. In preferred embodiments, the agent downregulates a cdc25A phosphatase and/or a cdc25B phosphatase.

The method is applicable to cells both in vitro and in vivo. For instance, the present application specifically contemplates the use of the method for reducing apoptotic cell death in an animal by administering to the animal an amount of an agent sufficient for inhibiting cdc25-dependent apoptosis, wherein the agent inhibits, e.g., one of expression of a cdc25 phosphatase, or a phosphatase activity of the cdc25 phosphatase, or reduces the cellular half-life of cdc25. According to the present invention, the subject method can be used in the treatment of disorders in animals, e.g., mammals, e.g., humans. Illustrative embodiments include utilizing the apoptosis regulating composition of the invention in the treatment of, for example, retrovirus-related disease including AIDS, ARC (AIDS related complex), ATL (adult T cell leukemia), hairy cell leukemia, myelopathy (HAM/TSP), respiratory disorder (HAB/HABA), arthropathy (HAAP), HIV- or HTLV-I (human T cell leukemia virus type I)-related diseases such as uveitis (HAU), and C-type hepatitis; autoimmune diseases including collagen diseases such as SLE (systemic lupus erythematosus) and rheumatoid arthritis (RA), ulcerative colitis, Sjogren's syndrome, primary biliary hepatic cirrhosis, idiopathic thrombocytopenic purpura (ITP), autoimmune hemolytic anemia, myasthenia gravis, Hashimoto's disease and insulin dependent (type I) diabetes mellitus; diseases accompanied by thrombocytopenia, for example, myelodysplastic syndrome (MDS), periodic thrombocytopenia, aplastic anemia, idiopathic thrombocytopenia and disseminated intravascular coagulation; liver diseases such as viral or drug-induced hepatitis (such as types C, A, B, and F) and hepatic cirrhosis; neurodegenerative disorders, such as Alzheimer's disease (AD), Huntington's disease (HD) and Parkinson's disease; myocarditis; ARDS (adult respiratory distress syndrome); infectious diseases; prostatic hypertrophy; uterine myoma; bronchial asthma; arteriosclerosis; congenital malformations; nephritis; senile cataract; chronic fatigue syndrome (CFS); and myotonic dystrophy.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press, 1989); *DNA Cloning,* Volumes I and II (D. N. Glover ed., 1985); *Oligonucleotide Synthesis* (M. J. Gait ed., 1984); Mullis et al., U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al., eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

DESCRIPTION OF THE FIGURES

FIG. 2 is the sequence for F1 and F2 Myc/Max binding fragments.

FIG. 3 is a comparison of the Myc/Max binding sites within the cdc25A (A1, A2 and A3), cdc25B (B1), prothymosine (PT; Gaubatz et al. (1994) *Mol. Cell. Biol.* 14:3853–3862) and ornithine decarboxylase (ODC; Bello-Fernandez et al. (1993) PNAS 90:7804–7808). The consensus sequence for Myc binding is provided for the cdc25 gene sequences, as well as for the broader comparison with the ODC and PT genes.

DETAILED DESCRIPTION OF THE INVENTION

Figure 1:
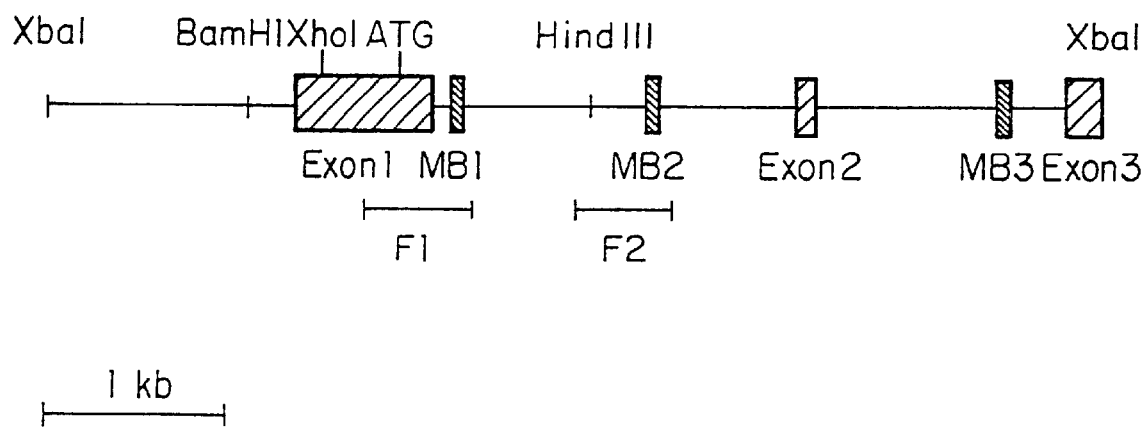
FIG. 1 is a schematic map of the human genomic cdc25A clone (12E). MB1, MB2 and MB3 show positions of the Myc-binding sites. F1 and F2 correspond to the Myc/Max binding fragments, identified by the modified precipitation assay (see Example 3).

Programmed cell death (apoptosis) is an active process by which cells initiate their own self-destruction. Apoptotic death is characterized by chromatin condensation and disassembly of the nuclear lamina, processes that are also characteristic of mitosis. The apparent similarity between the two events has led to the suggestion that apoptosis could be a defective form of mitosis, e.g., a catastrophic reentry into the cell-cycle. The present invention derives from the discovery that overexpression of cdc25, a mitotic activator, is capable of inducing apoptosis in various cells.

In previous studies (see, for example, U.S. Ser. No. 08/328,239) we observed oncogenic transformation of primary cells with an exogenous cdc25 gene in cooperation with an oncogenic form of the ras protein. In addition, oncogenic transformation was observed in Rb−/− cells by, for example, cdc25A alone. Cells transformed with cdc25 were highly aneuploid and were able to form colonies in soft agar and tumors in nude mice.

However, when cdc25 was recombinantly expressed alone in primary cell transfection experiments, we encountered difficulty in establishing stable clones. As described in the appended examples, overexpression of a cdc25 in those cells resulted in apoptotic death, which apoptosis apparently proceeds through a p53-dependent pathway. Moreover, we demonstrate that at least the cdc25A gene, and probably the cdc25B gene, are transcriptional targets upregulated by the myc pathway, indicating that the subject mechanism of cdc25-induced apoptosis is likely to be essential in myc-dependent cell-cycle stimulation and myc-induced apoptosis.

In hindsight, our findings now draw together recent observations as part of a coherent understanding for the role of cdc25 in both cellular transformation and apoptosis as part of a myc-dependent pathway. For instance, in addition to the finding that cdc25 cooperates with ras to transform cells, it has been observed that myc also cooperates with ras as a transformation mechanism. That a pathway interrelating myc and cdc25 exists is further supported by the observation that in various cancers a common phenotype of myc overexpression often has a parallel population of cdc25 overexpression. Finally, as described herein, the cdc25 gene is an apparent downstream transcriptional target for myc, supporting a biochemical basis for cdc25 involvement in myc-mediated events.

The present invention exploits our findings for cdc25 and makes available assays and reagents for identifying agents which inhibit cdc25-mediated mitotic activation. As described herein, anti-mitotic agents can be identified, in one embodiment of the present assay, through their ability to rescue an otherwise apoptotic cell from cell death by inhibiting the activity of an over-expressed cdc25 phosphatase, or the activity of at least one regulatory protein of the cell-cycle which acts as a mitotic activator of the cdc25 phosphatase activity. As set out in more detail below, overexpression of cdc25 in a non-transformation background (e.g. lack of ras overexpression or the like) can result in a generally apoptotic phenotype. Accordingly, normally quiescent cells (such as confluent normal fibroblasts) can be induced to undergo cell death in a cdc25-dependent manner. An agent which prevented mitotic activation by cdc25 could shift the phenotype from apoptotic back to quiescent. Accordingly, the assay provides a convenient read-out which is amenable to high throughput.

The term "apoptotic cell" denotes a cell having an impaired cell-cycle due to the overexpression of an exogenous cdc25 gene (e.g., recombinant), which impairment causes premature progression of the cell though at least a portion of the cell-cycle and thereby results in death of the cell. The phenomenon of apoptosis is well known, and can be described as a programmed death of cells. As is known, apoptosis is contrasted with necrosis, a phenomenon when cells die as a result of being killed by a toxic material, or other external effect. Apoptosis involves chromatic condensation, membrane blebbing, and fragmentation of DNA, all of which are generally visible upon microscopic examination.

In general, it will be expected that in order to detect an anti-mitotic agent in the present assay the agent must inhibit the cdc25 activity, or a cdc25 activator whose operation in the cell-cycle is sufficiently connected to the upregulation of cdc25 activity that the cell is prevented by the agent from committing to the otherwise catastrophic events induced by the overexpression of the phosphatase. In other words, it is clear that a useful agent effective at rescuing the apoptotic cell in the present assay can do so by acting directly on the exogenous cdc25, such as a phosphatase inhibitor, or alternatively, the agent may exert its effect by preventing the activation of cdc25, as, for example, inhibiting the phosphorylation step which activates cdc25 as a phosphatase.

In a preferred embodiment, a population of eukaryotic cells which are capable of undergoing cdc25-induced apoptosis is transfected with a recombinant gene coding for a cdc25 phosphatase. It will generally be desired that the cdc25 gene be of mammalian origin, especially human. For instance, an expression vector providing a human cdc25A gene, as described in the examples below, is most preferred. Sequences for a variety of cdc25 phosphatases which may be active in the present assay are generally known in the art. For example, Sadhu et al. (1990) *PNAS* 87:5139–5143, Galaktionov and Beach (1991) *Cell* 67:1181–1194, and Nagata et al. (1991) *New Biol.* 3:959–968 describe the cloning of three human cdc25 genes. Likewise, other mammalian cdc25 genes have been reported, such as from mouse (c.f., Wu et al. (1995)*Dev Biol* 170:195–206; Sebastian et al. (1993) *Proc Natl Acad Sci USA* 90:3521–4; and Kakizuka et al. (1992) *Genes Dev* 6:578–90) and pig (Cui et al. (1995) *J Anim Sci* 73:630). Moreover, it will be appreciated, based on the high sequence homology observed to date, that other orthologous genes to each of the human cdc25 genes can be cloned from non-human animals, especially other mammals.

Moreover while constitutive transcriptional regulatory elements can be used to drive expression of the recombinant cdc25 gene, it will typically be more advantageous to provide the gene as an inducible expression system. In the latter embodiment, the recombinant host cells can be maintained in culture without deleterious effects of cdc25 overexpression until which time as they are to be used to generate the subject assay. Those skilled in the art will recognize a variety of inducible eukaryotic promoters which can be used to control expression of the recombinant cdc25 gene. For example, such transcriptional control systems include those responsive to heavy metal ions (Mayo et al. (1982) *Cell* 29:99–108; Brinster et al. (1982) *Nature* 296:39–42; Searle et al. (1985) *Mol. Cell. Biol.* 5:1480–1489), heat shock (Nouer et al. (1991) in *Heat Shock*

*Response,* ed. Nouer, L., CRC, Boca Raton, Fla., pp167–220) or hormones (Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604).

In yet another approach, regulatory elements from evolutionarily distant species such as *E. coli* can be introduced into higher eukaryotic cells with the anticipation that effectors which modulate such regulatory circuits will be inert to eukaryotic cellular physiology and, consequently, will not elicit pleiotropic effects in eukaryotic cells. For example, the Lac repressor (lacR)/operator/inducer system of *E. coli* functions in eukaryotic cells and can be used to regulate cdc25 gene expression by three different approaches: (1) prevention of transcription initiation by properly placed lac operators at promoter sites (Hu & Davidson (1987) *Cell* 48:555–566; Brown et al. (1987) *Cell* 49:603–612; Figge et al. (1988) *Cell* 52:713–722; Fuerst et al. (1989) *Proc. Natl. Acad. Sci. USA* 86:2549–2553: Deuschle et al. (1989) *Proc. Natl. Acad. Sci. USA* 86:5400–5405); (2) blockage of transcribing RNA polymerase II during elongation by a LacR/operator complex (Deuschle et al. (1990) *Science* 248:480–483); and (3) activation of a promoter responsive to a fusion between LacR and the activation domain of herpes simples virus (HSV) virion protein 16 (VP16) (Labow et al. (1990) Mol. Cell. Biol. 10:3343–3356; Baim et al. (1991) *Proc. Natl. Acad Sci. USA* 88:5072–5076). In one version of the Lac system, expression of lac operator-linked cdc25 sequences is constitutively activated by a LacR-VP16 fusion protein and is turned off in the presence of isopropyl-$\beta$-D-thiogalactopyranoside (IPTG) (Labow et al. (1990), cited supra).

In still another exemplary embodiment (described in the examples below) components of the tetracycline resistance system of *E. coli* are used to regulate recombinant cdc25 gene expression. For example, the Tet repressor (TetR) can been fused to the activation domain of VP16 to create a tetracycline-controlled transcriptional activator (tTA) (Gossen et al. (1992) *Proc. Natl. Acad. Sci. USA* 89:5547–5551). The tTA fusion protein is regulated by tetracycline, i.e., tTA binds to tet operator sequences in the absence of tetracycline but not in the presence of tetracycline. Thus, in this system, in the continuous presence of tetracycline, gene expression is kept off, and to induce transcription, tetracycline is removed.

In preferred embodiments, the host cell which is used to generate the recombinant cell for the subject assay is a mammalian cell, most preferably a human cell, which can undergo cdc25-mediated apoptosis. Moreover, of mammalian cells which are useful in the present assay, normal diploid cells are most preferred. Exemplary reagent cells can be derived from, for example, such normal diploid cells as primary fibroblasts. However, we have observed that the subject assay can be derived generally with cells which are sensitive to myc-dependent apoptosis or, in some embodiments, E1A-dependent apoptosis, regardless of whether the host cell is a normal diploid cell or not. In many embodiments, though as an optional step, it will also be desirable that the cells be able to grow to confluence.

There are a variety of techniques available in the art for detecting the effects of a test compound on rescuing the apoptotic cell of the present invention. For instance, the level of apoptosis can be assessed by measuring cellular DNA fragmentation, such as by detection of nucleosomal-length DNA fragments on agarose electrophoretic gels (see e.g., Quingsheng et al. (1991) *Cell* 67:629–639). Other suitable assays of apoptosis include uptake of Hoechst 33342 dye (see e.g., Hardin et al. (1992) *J. Immunol. Methods* 154:99–107), detection of nuclear DNA damage using the intercalating dye p-phenylenediamine (see e.g., Salcedo et al. (1992) *J. Immunol. Methods* 148:209–216) and flow cytometry assays as described in Darzynkiewicz, Z. et al. (1992) Cytometry 13:795–808.

Thus, as an illustration of the subject assay in practice, agents able to modulate cdc25-mediated mitotic activation can be identified by the steps of (i) providing a population of test cells comprising a recombinant cdc25 phosphatase gene, which gene is expressible to levels in the cell which can cause apoptosis; (ii) contacting the test cell population with a candidate agent under conditions wherein the recombinant cdc25 phosphatase gene is expressed; (iii) determining the amount of cell death in the presence of the candidate agent; and (iv) comparing the amount of cell death in the presence of the candidate agent to an amount of cell death occurring in the absence of the candidate agent. A statistically significant change in the level of cell death occurring in the presence of the candidate agent is indicative of an agent which modulates cdc25-mediated mitotic activation. Agents to be tested for their ability to act as cdc25 inhibitors (or potentiators) can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide or analog thereof, preferably having a molecular weight of less than about 2,000 daltons.

In yet another embodiment, rather than detect cell death per se, the assay can be generated to evolve a detection signal from the expression or modification of a cellular protein effected by the activation of apoptotic mechanisms through overexpression of cdc25. Such indirect measurement of activation of the apoptotic pathway by cdc25 overexpression can be accomplished by detecting a biological activity modulated by the downstream effects of the phosphatase activity. As provided in the examples below, one apoptotic pathway induced by cdc25 overexpression is a p53-dependent pathway. Accordingly, a variety of techniques can be employed to detect the upregulated response of p53 in the recombinant cdc25 cell, or of another downstream target of cdc25 activation.

For example, the level of p53 can be detected directly, such as by immunoassay techniques (including immunoprecipitation/SDS-PAGE) using anti-p53 antibodies (e.g., anti-p53 (human) antibody is available as PharMingen catalog Nos. 14091A and 14211A). In an exemplary assay, normal fibroblast overexpressing cdc25 are contacted with a test agent, harvested, and lysed by standard techniques. The p53 protein levels in the cell sample are determined by immunoassay, and compared against p53 levels in untreated cells.

However, it will be clear to those skilled in the art that the use of antibodies in these assays is merely illustrative of binding molecules in general, and that the antibodies are readily substituted in the assay with any suitable molecule that can specifically detect p53. To further illustrate, certain of the natural binding partners of p53 can be used in place of an antibody to detect the presence of p53 in a cell. For example, the proteins MDM2 (Barak et al. (1992) *EMBO J* 11:2115; and Oliner et al. (1992) *Nature* 358:80) or WBP1 (Bischoff et al. PCT publication WO095/14777) can be substituted as p53-binding molecules for quantitating the level of p53 in a cell sample.

Moreover, rather than score p53 protein levels, other downstream targets p53 activation can be used in the detection step. For example, the level of p21$^{waf1}$ is dependent (upregulated) on the activation of p53 and consequently can also be used to determine the ability of a test compound to modulate cdc25 mitotic activation.

This embodiment of the subject assay in practice, provides for the identification of agents able to modulate cdc25-mediated mitotic activation by the steps of (i) providing a population of test cells comprising a recombinant cdc25 phosphatase gene preferably, though optionally, inducible, which gene is expressible to levels in the cell which can cause apoptosis; (ii) contacting the test cell population with a candidate agent under conditions wherein the recombinant cdc25 phosphatase gene is expressed; (iii) determining the cellular level of a protein which is modulated by cdc25-mediated apoptosis, e.g., a p53 protein and/or a p21 protein; and (iv) comparing the level of that protein in the presence of the candidate agent to the level occurring in the absence of the candidate agent. A statistically significant decrease in level of expression of p53, for example, relative to a level of expression in the absence of the candidate agent, is indicative of an inhibitor of cdc25-mediated mitotic activation.

In yet an another embodiment of the subject assay, the means for detecting p53 comprises, for example, a reporter gene construct which includes a transcriptional regulatory element which binds and is responsive to the p53 protein. The gene product is a detectable label, the signal from which is dependent in dose-dependent manner on the level of p53 in the cell. Exemplary reporter genes include enzymes, such as luciferase or β-galactosidase which can produce a spectrometrically active label, or a gene product which alters a cellular phenotype, e.g., drug resistance or auxotrophy.

An exemplary reporter gene construct comprises a luciferase gene whose expression is driven by the core Herpes simplex virus thymidine-kinase (TK) promoter which has been modified with a p53 responsive element (p53RE/TK). See, for example, U.S. Pat. No. 5,362,623. When a version of the construct lacking any of the modifications to the TK promoter is transfected into mammalian cells, the detectable luciferase activity is low because this core TK promoter fragment does not contain the upstream activating sequences necessary for efficient transcriptional activation of the luciferase gene. However transfection with the constructs in which TK is further modified to contain either 3 or 6 response-elements (RE) for p53, the detectable luciferase activity increases in cells in a dose-dependent manner relative to p53 levels.

The p53RE/TK vector is transfected into a p53$^+$ cell-line which is capable of over-expressing an exogenous cdc25 gene. Luciferase expression is upregulated by the presence of p53, which functions as a transcriptional activating factor by binding to the p53 response element upstream of the TK promoter. Measurement of luciferase activity can be carried out by standard protocols (see, for example, Promega Technical Bulletin #TB161). Cells are grown and transfected in a tissue culture grade 96 well microtitre plate. The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay substrate (Beetle luciferin, Promega catalog no. E1603) is added, and the reaction in each well monitored in a luminometer or scintillation counter. Upregulation of the p53 system results in a greater luminescence signal than the uninduced system. A salient feature of this assay is that, although it is an in vivo assay, this screen will ignore general cytotoxic compounds.

As an illustration of the subject assay in practice, agents able to modulate cdc25-mediated mitotic activation can be identified by the steps of (i) providing a population of test cells comprising a recombinant cdc25 phosphatase gene, and a reporter gene under transcriptional control of a p53 responsive element; (ii) contacting the cell with a candidate agent under conditions wherein the recombinant cdc25 gene is expressed; (iii) detecting the level of expression of the reporter gene; and (iv) comparing the measured level of reporter gene expression in the presence of the candidate agent with a level of expression in the absence of the candidate agent. A statistically significant decrease in level of expression of the reporter gene, relative to a level of expression in the absence of the candidate agent, is indicative of an agent which inhibits cdc25-mediated mitotic activation.

Another aspect of the present invention relates to the diagnostic value of our discovery that at least cdc25A is involved in apoptosis of cells. In particular, the level of expression of a cdc25 gene product can be used to determine the pathology of tissue death, e.g., to discern between apoptotic phenotypes and necrosis, as well as to assess the risk of an individual for having a disorder marked by apoptotic cell death.

To illustrate, nucleotide probes can be generated from the subject cdc25 genes which facilitate histological screening of intact tissue and tissue samples for determining the abundance of cdc25-encoding transcripts. Used in conjunction with immunoassays for detecting cdc25 protein levels, the oligonucleotide probes can help- facilitate the determination of the molecular basis for a disorder marked by cell death, e.g., which may involve some abnormality associated with over-expression of an cdc25 protein. For instance, variation in polypeptide synthesis and/or stability can be differentiated from overexpression caused at the transcriptional level.

Accordingly, the present method provides a method for determining if a subject is at risk for a disorder characterized by aberrant cell death. In preferred embodiments, method can be generally characterized as comprising detecting, in a sample of cells from the subject, the overexpression of a cdc25 gene, preferably a cdc25A gene. To illustrate, such lesions in cdc25 expression can be detected by ascertaining the existence of at least one of a gross alteration in the level of a messenger RNA transcript of a cdc25 gene, and/or a non-wild type level of an cdc25-protein. As set out below, the present invention provides a large number of assay techniques for detecting lesions in a cdc25 gene which result in overexpression of a cdc25 protein, and importantly, provides the ability to discern between different molecular causes underlying cdc25-dependent aberrant cell death.

In an exemplary embodiment, there is provided a nucleic acid composition comprising a (purified) oligonucleotide probe including a region of nucleotide sequence which is capable of hybridizing to a sense or antisense sequence of a cdc25 gene transcript, such as an MRNA encoding cdc25A. The MRNA transcripts of a cell(s) is rendered accessible for hybridization, such as by purification using the method of Chomczynski (described in U.S. Pat. No. 4,843,155). The probe is exposed to nucleic acid of the sample, and the hybridization of the probe to the sample nucleic acid is detected. In preferred embodiments, the probe is labeled for detection. Exemplary labels include radioisotopes, fluorescent compounds, enzymes, and enzyme co-factors.

In still another embodiment, the level of an cdc25 protein can be detected by immunoassay. For instance, the cells of a biopsy sample can be lysed, and the level of an cdc25 protein present in the cell can be quantitated by standard immunoassay techniques. As above, in preferred embodiments, the anti-cdc25 antibody is labeled to facilitate detection.

Yet another aspect of the present invention relates to our observation that myc is a transcriptional regulator of cdc25 genes. For instance, as set forth in the appended examples, we observed that expression of the hormone inducible c-myc estrogen receptor chimera resulted in activation of cdc25A. To our knowledge, this is the first demonstration of a physiologically relevant gene which is actually transcriptionally regulated by myc. Accordingly, the present invention provides novel transcriptional regulatory elements which are capable of directing expression of a gene in response to activation by a myc transcriptional factor.

Based on the identification of myc specific-DNA-binding fragments ("myc-responsive transcriptional regulatory element" or "myc-RE"), a number of diagnostic and therapeutic methods have been devised. According to one such method, the level of myc expression, or the expression of mutant forms of the protein, can be tested by virtue of its specific DNA binding ability. It is known for various cancers and stages of cancers that myc is overexpressed or, alternatively, that one or both of the myc alleles in tumor tissues is mutant. Detecting the presence or absence of wild-type myc protein can provide diagnostic and prognostic information regarding a tumor and the patient. Likewise, myc expression can be used to access the mechanism or risk of cellular apoptosis, or detect myc dysfunction in various differentiative disorders.

Although any method can be employed which utilizes the myc-specific DNA binding sites of the present invention, two exemplary methods are disclosed for ascertaining myc-specific DNA binding. According to one method, myc specific-DNA-binding fragments, such as derived from the cdc25A gene, are incubated in the presence of a test mixture, e.g., a cell lysate. The amount of myc protein bound to the nucleic acid can be assessed, such as by immunoassay, etc.

In another embodiment, utilizing the myc-RE sequences of a cdc25 gene, e.g., the myc responsive sequences of the cdc25A or cdc25B genes, a reporter construct can be generated from which a reporter gene's expression is controlled at least in part by myc. Such constructs can be subsequently employed to generate a recombinant cell which provides a convenient readout of the level of myc in the cell. For example, as with the p53RE construct described above, an isolated portion of the cdc25A gene including the myc-responsive regulatory element(s) can be used to drive expression of a reporter gene in a myc-dependent manner. Thus, transfection of a biopsied cell sample from a patient with such a myc-dependent reporter construct can provide information pertaining to the state of the cells in the cell sample. The presence or absence of myc gene products can also be detected in body samples, such as, serum, stool, or other body fluids, such as urine and sputum.

The term "isolated" as also used herein with respect to nucleic acid comprising a myc-responsive regulatory sequence refers to molecules separated from other nucleic acid that are present in the natural source of cdc25 gene. For example, an isolated myc-responsive regulatory sequence includes no more than 10 kilobases (kb) of nucleic acid sequence which naturally immediately flanks the myc-RE in a cdc25 gene in genomic DNA, more preferably no more than 5 kb of such naturally occurring flanking sequences, and most preferably less than 2.5 kb of such naturally occurring flanking sequence.

As described in Example 3, we have identified myc/max binding sites within genomic human cdc25A and cdc25B genes. Based on these results, a core consensus sequence for the cdc25 myc-RE is CAYGTG, embedded in the longer consensus sequence of WGNCAYGTGCNNNNMNNNMC-SRR. Alternatively, comparison of the cdc25 sequence with other myc binding elements known in the art suggests a consensus sequence of SNNSNGNCAYGTG-SYNNNMNNNCSNR. Accordingly, the reporter gene construct can be generated to include at least the core consensus sequence CAYGTG, though longer portions of the cdc25 genomic sequence can be used. For example, fragments of a cdc25 genomic sequence of at least 25, 50, 75, 100 or 125 nucleotides in length, and which include one or more myc binding sites, may be used. For instance, the reporter gene construct can be generated to include a myc-RE provided in the form of a fragment of a cdc25A gene corresponding to the F1 or F2 fragments (see FIG. 2). Alternatively, the complete cdc25A intron in which the three myc-responsive elements (MB1-MB3) occur, or a fragment thereof including at least one or both of MB1 and MB2, can be provided in the reporter construct.

To derive the reporter construct, a nucleic acid sequence including a myc-RE is operably linked to the reporter gene such that it participates in the transcriptional regulation of the reporter gene. For example, the myc responsive element can be provided in the 5' flanking sequence of the reporter gene, e.g., upstream of the reporter gene coding sequence. In an alternate embodiment, the myc-RE can be provided, as in the cdc25 gene, as part of an intronic sequence which disrupts the coding sequence for the reporter gene, but which is spliced out of the transcript to form a mature mRNA. To illustrate, the intronic sequence of the cdc25A gene, e.g., which includes MB1 and MB2, is ligated into the coding sequence of the reporter gene. The intronic sequence provides, in addition to the myc responsive elements, 5' and 3' splice sites along with a branch point. By routine manipulation of the ligation site, the resulting transcript will splice out the cdc25A intron, and resplice the 5' and 3' exons of the reporter gene in frame. Considerations and techniques for addition of exogenous intronic sequence to a coding sequence are known in the art.

In yet another embodiment, the reporter gene is provided in the form of a genomic cdc25 gene. According to this embodiment, the reporter gene is a cdc25 gene which includes at least those intronic sequences providing myc responsiveness. For example, the reporter gene can include the cdc25A coding sequence, along with intron 1 (e.g., which includes MB1 and MB2) as well as, optionally, intron 2 (see FIG. 1). The expression of the cdc25 reporter gene can be detected, for instance, by use of synthetic substrate such as p-nitrophenylphosphate (pNPP), 3-O-methyl-1-fluorescein monophosphate (MFP) or fluorescein diphosphate (FDP) according to the methods described in the Beach U.S. Pat. No. 5,294,538 and/or Galaktionov and Beach (1991) Cell 67:1181–1194. Mitotic activation, or apoptosis, caused by expression of the cdc25 gene can also be used as a readout.

In still another embodiment, the reporter gene can be a chimeric gene comprising at least the 5' portion of the genomic sequence of a cdc25 gene fused to a sequence encoding a detectable protein, e.g., an enzyme or an antigenic epitope. In an illustrative embodiment, a portion of the human cdc25A genomic sequence corresponding to exons 1 and 2 and intron 1 are ligated to the 5' end of sequence encoding glutathione-s-transferase (GST) such that the coding sequence of exon 2 is in frame with the coding sequence for the GST protein. Expression of the cdc25/GST fusion protein can be detected using antibodies to the GST portion of the protein, or by detecting the GST activity using 1-chloro-2,4-dinitrobenzene (Habig et al (1974) *J Biol Chem* 249:7130).

Such fusion proteins may also be useful for isolating the reporter protein from a cell lysate, e.g., using a glutathione-derivatized matrices, then quantitating the level of expression by detecting intrinsic activity of the cdc25 portion of the fusion protein. See, for example, the Beach U.S. Pat. No. 5,294,538.

Yet another embodiment of the reporter construct provides the reporter gene as part of a polycistronic message with a cdc25 genomic sequence. For example, a bicistronic message can be generated from a transcript provided by tandemly arranging, 5' to 3', a genomic cdc25 gene sequence, e.g., which includes myc-responsive elements, a reporter gene, and a short non-coding linker between the two. In preferred embodiments, the cdc25 coding sequence can be mutated to provide a enzymatically inactive form of the protein, e.g., such as C473S cdc25B mutant or the like, in order to prevent adverse effects to the cell upon expression of the phosphatase.

As a result of the discoveries of the present invention, screening methods are provided to isolate chemical agents which may have use in regulating various proliferative and differentiative events in cells. Specifically, agents can be screened for the ability to affect myc binding and/or transcriptional activation of genes by myc transcriptional complexes. The necessary components for such a screening method are provided by this invention and include nucleic acid molecules which contain a myc-RE sequence as described herein.

One such screening method is a binding assay in which the amount of binding of a myc protein to a nucleic acid molecule which comprises the binding site (or a conforming sequence) is measured. The amount of binding is also measured for a myc protein in the presence of a test substance. If the test substance modulates (e.g., inhibits or potentiates) the amount of myc binding in a statistically significant manner, then the test substance is a candidate for use in altering the proliferation, differentiation or death of a cell. Methods for measuring the amount of binding can be any of which are known in the art (c.f., Tan et al (1990) *Cell* 62:367–377). One particular method employs immunoprecipitation. Briefly, purified myc/max (or max/max) complexes, or a lysate of a cell expressing both proteins is incubated with radiolabeled DNA and anti-myc antibodies under conditions where proteins bind to DNA. Protein A-Sepharose and poly-dIdC-poly-dIdC are then added for an additional incubation. A pellet is formed and washed and the proteins are removed by digestion with a protease, and DNA is obtained by phenol extraction. The extracted DNA is then analyzed by electrophoresis and quantified. Quantitation of the DNA can be by autoradiography, for example. The amount of DNA immunoprecipitated is proportional to the amount of binding of the myc protein complex to the DNA.

In yet another embodiment, a reporter construct as described above can be used to determine the effect of a candidate agent on myc-dependent transcriptional activation, e.g., by detection of a reporter gene product expressed in the presence and absence of a test compound.

In an illustrative embodiment, to construct a myc-RE/luciferase reporter construct, the pGL3-Basic vector (Promega) is modified by addition, in the multiple cloning region, of a restriction fragment containing at least one myc-RE of the transcriptional regulatory sequence of a cdc25 gene. The resulting construct is subsequently used to transfect mammalian cells following the manufacturer's suggests (Technical notes, Part #TM003 of Promega Catalog no. E164). The myc-RE vector is transfected into a cell-line which expresses both the myc and max proteins. Luciferase expression is upregulated by myc-dependent transcriptional complexes, which bind to the myc response element upstream of the reporter gene and activate expression of that gene. Measurement of luciferase activity can be carried out by standard protocols (see, for example, Promega Technical Bulletin #TB161). The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay substrate (Beetle luciferin, Promega catalog no. E1603) is added, and the reaction in each well monitored in a luminometer or scintillation counter. Down regulation of myc-induced expression by a test agent results in a statistically significant decrease in luminescence signal relative to the control system (no test compound).

Moreover, the present invention provides a method for inhibiting myc-dependent alterations in cellular phenotype, such as myc-dependent apoptosis. As described in the appended examples, the cdc25A and cdc25B genes are apparent transcriptional targets of the myc protooncogene. Coupled with the observations herein of cdc25-induced apoptosis, cdc25 gene products are deemed to be physiologically significant mediators of myc function. The subject method counteracts cdc25 induction by myc by modulating, for example, one or more of cdc25 expression, protein stability, phosphatase activity and/or interaction of cdc25 with other cellular factors. For example, myc-dependent apoptosis can be prevented by inhibiting cdc25 expression by antisense, or by the use of agents which inhibit formation of productive myc transcriptional complexes with myc-responsive elements of a cdc25 gene. In other embodiments, myc-dependent apoptosis may be inhibited by use of agents which directly inhibit the phosphatase activity of a cdc25, or which prevent its activation. The subject method is applicable both in vitro, e.g., in cell culture, and in vivo, e.g., in the treatment of neurodegenerative disorders or modification of immune responses.

The apoptosis regulating compositions and methods of this invention can regulate or control apoptosis and, because of this action, can be suitably used in the treatment of various diseases. Specifically stated, the apoptosis regulating composition of the invention can be used in the treatment of, for example, retrovirus-related disease including AIDS, ARC (AIDS related complex), ATL (adult T cell leukemia), hairy cell leukemia, myelopathy (HAM/TSP), respiratory disorder (HAB/HABA), arthropathy (HAAP), HIV- or HTLV-I (human T cell leukemia virus type I)-related diseases such as uveitis (HAU), and C-type hepatitis; autoimmune diseases including collagen diseases such as SLE (systemic lupus erythematosus) and rheumatoid arthritis (RA), ulcerative colitis, Sjogren's syndrome, primary biliary hepatic cirrhosis, idiopathic thrombocytopenic purpura (ITP), autoimmune hemolytic anemia, myasthenia gravis, Hashimoto's disease and insulin dependent (type I) diabetes mellitus; diseases accompanied by thrombocytopenia, for example, myelodysplastic syndrome (MDS), periodic thrombocytopenia, aplastic anemia, idiopathic thrombocytopenia and disseminated intravascular coagulation; liver diseases such as viral or drug-induced hepatitis (such as types C, A, B, and F) and hepatic cirrhosis; neurodegenerative disorders, such as Alzheimer's disease (AD), Huntington's disease (HD) and Parkinson's disease; myocarditis; ARDS (adult respiratory distress syndrome); infectious diseases; prostatic hypertrophy; uterine myoma; bronchial asthma; arteriosclerosis; congenital malformations; nephritis; senile cataract; chronic fatigue syndrome (CFS); and myotonic dystrophy.

In an exemplary embodiment, subject method can be employed with cells propagated in culture. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, cultured neuronal cells can undergo apoptosis, resulting in loss of cells from the culture. This is commonly observed when they are grown in culture from adult tissue. By preventing cdc25-dependent apoptosis in the culture, the integrity and longevity of the culture can be extended. For example, the present method can be used in vitro to maintain the differentiation of glial cells, schwann cells, chromaffin cells, cholinergic sympathetic or parasympathetic neurons, as well as peptidergic and serotonergic neurons. The subject therapeutic can be used alone, or can be used in combination with neurotrophic factors which act to more particularly enhance a particular differentiation fate of a neuronal cell.

In another aspect, the subject method is used to enhance survival of neurons and other neuronal cells in both the central nervous system and the peripheral nervous system. The ability to regulate apoptosis can be important in the control of adult neurons with regard to maintenance, functional performance, and aging of normal cells; repair and regeneration processes in chemically or mechanically lesioned cells; and prevention of degeneration and premature death. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflamatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration and apoptotic death of discrete populations of neuronal elements and may be treatable by the present method. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of therapeutics which inhibit cdc25-dependent apoptosis, in order to control apoptotic events which give rise to loss of neurons (e.g. to enhance survival of existing neurons).

In addition to degenerative-induced dementias, the subject method can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. The dying striatal neurons exhibited all of the morphological and biochemical hallmarks of apoptosis. Ballism is typically associated with damage to the subthalamic nucleus, often due to acute vascular accident.

Also included in the subject treatment are neurogenic and myopathic diseases which ultimately affect the somatic division of the peripheral nervous system and are manifest as neuromuscular disorders. In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The subject method can be used alone, or in conjunction with neurotrophic factors such as CNTF, BDNF or NGF to prevent and/or reverse motor neuron degeneration in ALS patients.

The apoptosis regulating method of the present invention can also be used as a cirrhosis preventive treatment which controls apoptosis in patients with drug-induced hepatitis or viral hepatitis to thereby manifest a therapeutic effect in hepatitis and prevent hepatocytes from fibrogenesis.

In one embodiment, the subject method relies on the use of isolated nucleic acid in "antisense" therapy in order to prevent cdc25-dependent apoptosis. As used herein, antisense therapy refers to administration or in situ generation of oligonucleotide probes or their derivatives which specifically hybridize (e.g. binds) under cellular conditions with the cellular mRNA and/or genomic DNA encoding a cdc25 phosphatase, such as cdc25A or cdc25B, so as to inhibit expression of that protein, e.g. by inhibiting transcription and/or translation. By this definition of antisense, nucleic acids which bind to myc-RE sequences and prevent the association of myc transcriptional complexes with the cdc25 gene are also contemplated. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

In a preferred embodiment, the antisense nucleic acid specifically hybridizes to a cdc25A nucleic acid, e.g., a human cdc25A mRNA or genomic cdc25A sequence. By specifically hybridize, it is meant that the antisense nucleic acid, when bound to a cellular nucleic acid by base-pairing, exhibits at least ten fold less binding to nucleic acid which is not a cdc25A nucleic acid (e.g. "background" or "nonspecific" hybridization), more preferably at least 100 fold, and even more preferably 1000 fold less background hybridization.

An antisense construct of the present invention can be delivered, for example, as an expression plasmid which, when transcribed in the cell, produces RNA which is complementary to at least a unique portion of the cellular mRNA which encodes a cdc25 protein. Alternatively, the antisense construct is an oligonucleotide probe which is generated ex vivo and which, when introduced into the cell, causes inhibition of expression by hybridizing with the mRNA and/or genomic sequences encoding the cdc25 protein. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775) and peptide-nucleic acids. Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

In another embodiment, the anti-apoptotic therapeutic is a compound which directly inhibits the phosphatase activity of a cdc25, or which inhibits the activation of the cdc25 phosphatase by some allosteric mechanism. For purposes of illustration, the subject method can be carried out using such cdc25 inhibitors as benzoquinoid compounds. For example, dnacin A1 (R=CN) and dnacin B1 (R=OH),

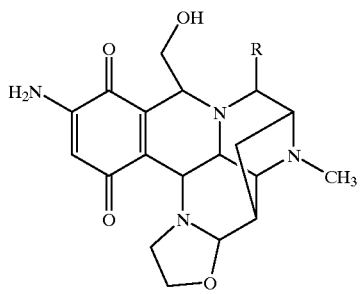

have previously been described in the literature as cdc25 inhibitors. The present invention contemplates the use of pharmaceutical formulations of dnacin or related benzoquinoids in the treatment of certain diseases characterized by cdc25-dependent apoptosis.

In therapeutic applications, the antiapoptotic agents of the present invention can be formulated for a variety of modes of administration, including systemic and topical or localized administration. Techniques and formulations generally may be found in *Remmington's Pharmaceutical Sciences*, Meade Publishing Co., Easton, Pa. For systemic administration, injection is preferred, including intracranial, intrathecal, intramuscular, intravenous, intraperitoneal, and subcutaneous for injection. The agents can be formulated in liquid solutions, preferably in physiologically compatible buffers such as Hank's solution or Ringer's solution. In addition, the agent may be formulated in solid form and redissolved or suspended immediately prior to use. Lyophilized forms are also included.

Systemic administration can also be by transmucosal or transdermal-means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

Exemplification

The invention now being generally described, it will be more readily understood by reference to the following examples which are included merely for purposes of illustration of certain aspects and embodiments of the present invention, and are note intended to limit the invention.

In rodent cells, human cdc25A or cdc25B but not cdc25C phosphatases cooperate with either Ha-ras(Val12) or loss of Rb in oncogenic focus formation. Such transformants are highly aneuploid, capable of growth in soft agar and form high grade tumors in nude mice. Overexpression of cdc25 occurs in human primary cancer. Breast cancer patients with overexpression of cdc25B have a higher recurrence rate and decreased disease-free survival. These results indicate that cdc25 overexpression in primary oncogenic lesions predicts poor prognosis and suggests that the cdc25 phosphatases play a role in human cancer.

The c-myc protooncogene is a key regulator of cell growth and differentiation, but despite considerable effort only the prothymosine and ornithine decarboxylase genes have been described as direct transcriptional targets that have been associated with positive regulation of cell growth (Packham et al. (1995) Biochim. Biophys. Acta 1242:11–28). Regulation of prothymosine by c-myc is cell type specific (Gaubatz et al. (1994) Mol. Cell. Biol. 14:3853–3862), but the gene displays no known oncogenic properties making it an unlikely candidate as a major c-myc target. Ornithine decarboxylase has been shown to transform 3T3 cells in vitro (Auvinen et al. (1992) Nature 360:355–358), however, domains of c-myc that are essential for interaction with Max and are required for both transformation and apoptosis appear to be dispensible for Myc induction of ODC (Packham et al., supra). In addition, small molecule inhibitors of the ODC enzyme only marginally affect myc-dependent apoptosis (Packham et al. (1994) Mol. Cell. Biol. 14:5741–5747). This suggests that ODC is unlikely to be the sole relevant target of Myc (Packham et al. (1995) Biochirn. Biophys. Acta 1242:11–28).

The following considerations, described in the examples below, lead us to submit that cdc25A is at least one physiologically relevant target of Myc. Firstly, cdc25A mRNA abundance is elevated following activation of Myc. Secondly, the cdc25A gene contains three functional Myc/Max binding sites within the first two introns, and these can direct Myc-dependent transcription from a heterologous promoter. Interestingly, Myc-binding sites have been found downstream of the transcription initiation site in all known Myc transcriptional targets, including ODC. Third, in the absence of adequate levels of growth factors, introduction of cdc25A into a responsive cell line causes p53-dependent apoptosis. Finally, myc-driven apoptosis was inhibited by cdc25A antisense oligonucleotides, suggesting that cdc25A expression is essential for apoptosis under these experimental conditions. We also observed that cdc25B is induced by MycER, although at a later time and to a lesser extent than cdc25A. A single DNA fragment carrying a Myc/Max binding site was found in the cdc25B gene. Thus, it is possible that cdc25A and cdc25B might act cooperatively in Myc-driven apoptosis.

These findings are also supported by a great deal of circumstantial evidence that point to a potential role of cdc25 as a mediator of myc function. Thus, c-myc has been shown to rapidly stimulate the activity of cyclin E and cyclin D1 dependent kinases (cdk2 and cdk4, respectively), without altering the protein levels of cdk2, cdk4, cyclin E or cyclin D1 (Steiner et al. (1995) EMBO J. 14:4814–4826). Cdc25 is a well-established activator of cyclin dependent kinases (Millar et al. (1992) Cell 68:407–410). Expression of cdc25A, which is essential for transition from G1 to S phase (Jinno et al. (1994) EMBO J. 13:1549–1556; and Hoffmann et al. (1994) EMBO J. 13:4302–4310), is known to be growth factor responsive, peaking as early as 3 hours after serum stimulation of quiescent fibroblasts (Jinno et al., supra). This coincides temporally with c-myc induction in the same cells (Waters et al. (1991) Oncogene 6:797–805), and thereafter the levels of both c-myc (Waters et al., supra) and cdc25A (Hoffmann et al., supra) are relatively constant during the cell cycle. The precise physiological substrates of cdc25A and B have yet to be formally established. However, cdk4 becomes tyrosine phosphorylated following UV irradiation and cdc25A can reverse this process (Terada et al. (1995) Nature 376:358–362). Although the role of cdk4 tyrosine phosphorylation in non-irradiated cells is unclear, cdk2 is clearly regulated by tyrosine phosphorylation in undamaged cells (Hoffmann et al., supra). A key substrate of both cdk4 and cdk2 kinases is the retinoblastoma protein (Sherr, C. J. (1994) Cell 79:551–555), and induction of Myc leads to Rb phosphorylation and inactivation (Steiner et al. (1995) EMBO J. 14:4814–4826; and Goodrich et al. (1992) Nature 360:177–179), presumably by the activated cdks. Finally, cdc25A and cdc25B are able to cooperate with Ha-ras in oncogenic transformation of normal rodent fibroblasts (Galaktionov et al. (1995) Science 269:1575–1577), a well known c-myc property (Land et al. (1983) Nature 304:596–602).

The proposed transcriptional cdc2A activator, Myc, appears to induce both DNA replication and apoptosis in the absence of growth factors. Myc-driven apoptosis is enhanced in the presence of wild type p53 (Hermeking et al. (1994) Science 265:2091–2093; and Wagner et al. (1994) Genes Dev. 8:2817–2830). Induction of Myc causes an elevation in the intracellular levels of p53 (Wagner et al., supra), which presumably contributes to Myc-driven apoptosis. We also consistently observed elevation of p53 levels upon cdc25A induction in A10 cells. However, cdc25A-driven apoptosis may occur to an extent in the absence of the wild type p53, probably indicating that p53 is not absolutely essential for the apoptosis caused by cdc25A.

While not wishing to be bound by any particular theory, we suggest two alternative mechanisms by which cdc25 might lead to p53 stabilization. In the absence of growth factors myc-driven cell cycle progression could lead to aberrant DNA replication that might be associated with a DNA damage, thus triggering stabilization of the p53 and subsequent apoptosis. An alternative pathway is suggested by our observation that cdc25 is degraded by the ubiquitin-mediated proteolysis in fission yeast. Interestingly, an E3 subunit, responsible for cdc25 degradation in fission yeast has significant homology to E6AP, an E3 enzyme involved in p53 degradation in the human cells. Thus, it is conceivable that Cdc25 might compete with p53 for some component of proteolytic machinery, causing accumulation of the p53 protein. If this happens to be the case, cdc25-driven apoptosis might not require cdk activation or DNA replication, and might be quite independent of the DNA damage response. Whatever the precise mechanism by which cdc25 triggers apoptosis and its relationship to p53, our results point to a role for the cell cycle phosphatases as a targets of c-myc in normal growth control, oncogenesis and apoptosis.

EXAMPLE 1

To investigate this possibility we introduced cdc25A, B, and C on a mammalian constitutive expression vector into normal mouse embryo fibroblasts at early passage. Cells were transfected with these plasmids either alone or in combination with oncogenic versions of Ha-ras (V12) or p53 (K258). The cells were then plated in either nonselective or selective (G418) media. After four to five weeks, the plates were stained and photographed to detect formation of the potentially transformed foci. G418-selected colonies were counted to assess transformation efficiency. In these assays we observed oncogenic cooperation between cdc25A or cdc25B and Ha-ras. Conversely, no cooperation between cdc25C and ras was detected. A few weak foci were formed upon transfection of cdc25A alone, and only slightly more were observed with the combination of cdc25A and mutant p53. No focus formation was observed with Ha-ras (V12) alone as has been previously described (Land et al. (1983) Nature 304:596–602; and Ruley et al. (1983) Nature 304:602–606). In all experiments, similar numbers of the G418 selected colonies were obtained. Clones isolated from the foci were found to mildly overexpress cdc25 proteins (2–3 fold).

Microscopical examination of the cdc25A/ras and cdc25B/ras foci revealed a transformed cell morphology, indicated by multilayer growth, loose attachment to the substrate and aneuploidy. Cells from individual foci readily grew in the presence of G418, demonstrating that they represent cells transfected with the plasmids rather than spontaneously transformed mouse cells. Cells cotransfected with cdc25A or cdc25B and Ha-ras (V12) together with relevant controls were tested for the ability to form colonies in soft agar. At three weeks we detected formation of tight colonies with cells derived from any of three independent foci of the ras/cdc25A or ras/cdc25B cotransfected cells. To verify the tumorigenic potential of these cells, they were introduced into nude mice. After 20–25 days we could detect clear tumor formation in all experimental animals injected with cdc25A/ras or cdc25B/ras transfected cells (in each case eight mice were injected). The average size of tumors at 25 days postinjection was 5.6±1.7 mm for cdc25A/ras and 7.4±2.5 mm for cdc25B/ras. No tumors were detected in mice injected with G418-selected cells that had been transfected with either ras or cdc25 alone or with the parental vector plasmid.

In human tumors, mutations in ras often coincide with mutations or deletions in the tumor supressor genes p53 and Rb1. As described above, human cdc25A and cdc25B cooperate with Ha-ras, but are weakly oncogenic when introduced alone into normal diploid cells. Therefore, we decided to investigate whether defects in p53 and Rb1 could render normal fibroblasts susceptible to the oncogenic effects of cdc25A overexpression. To pursue this further, we took advantage of the primary fibroblasts derived from mice with either Rb1 or p53 genes disrupted by targeted homologous recombination (Jacks et al. (1992) *Nature* 359:295–300; Livingstone et al. (1992) *Cell* 70:923–935; Jacks et al. (1994) *Curr. Biol.* 4:1–7).

In a series of transfection experiments, we introduced cdc25A into Rb–/– or p53–/– fibroblasts and after four weeks scored formation of the oncogenic foci. Focus formation was observed on the monolayer of Rb/– cellss. In the case of p53–/– cells we selected transformants with G418, since p53–/– cells overgrow upon periodic addition of fresh media and foci cannot be visually detected and scored on the background of untransfected cells. Rb–/– or p53–/– cells transfected with cdc25A or parental vector plasmid were further grown in the continuous presence of the G418 selection. Experiments assaying growth in soft agar and in nude mice demonstrated oncogenic properties of the cdc25A transfected Rb–/– cells but not p53–/– cells. All cells transfected with control plasmids were nononcogenic.

Because of strong in vitro evidence of cdc25 acting as an oncogene, we made a preliminary analysis of cdc25 expression in cell lines derived from various human tumors. This preliminary survey uncovered high levels of cdc25 expression in several cell lines, including cells originated from human breast cancer. Based on this observation, we investigated the expression of cdc25 in a previously characterized series of human primary breast cancers, to assess whether its oncogenic potential in vitro is accompanied in vivo by overexpression, and whether overexpression was predictive of recurrence and/or outcome. The study population (107 ductal, 12 lobular, 1 medullary, 2 papillary and 2 colloid carcinomas) consisted of a retrospective series of 124 axillary node-negative invasive breast cancer patients treated between 1972–1982. The patients were all treated by modified radical mastectomy, without perioperative adjuvant therapy and had a median follow-up of 11 years. These patients had previously been characterized in terms of size, histologic and nuclear grade, mitotic rate, peritumoral lymphovascular invasion, microvessel density, and p53 status (Le et al. (1992) *Mod Pathol* 5:61–67; Bosari et al. (1994) *J Natl Cancer Inst* 86:681–687; Bosari S et al. (1993) *Virchows Arch* A421:291–295; Bosari et al. (1992) *Hum. Pathol.* 23:755–761; Lee et al (1990) *J Clin Oncol* 8:1457–1465; Nasse et al. (1993) *Hum. Pathol.* 24:950–957).

Normal and neoplastic archival tissue was used for in situ hybridization utilizing antisense riboprobes for cdc25 A, B and C. There was no detectable expression of cdc25C in normal and tumor tissue. No detectable expression of cdc25B by in situ hybridization was seen in normal breast tissue. 32% of patients, however, overexpressed cdc25B in the neoplastic tissue and the remaining tumors expressed low or undetectable levels of this mRNA. In many tumors practically all cells displayed high levels of cdc25B mRNA, suggesting that both growth factor and cell cycle regulation of expression is disrupted further underscoring the deregulation of its expression. No correlation between the mitotic index of the particular tumor and cdc25B overexpression was found (p=0.849).

To further investigate the significance of the observed tumor-specific cdc25 overexpression, we correlated cdc25B expression with other tumor-specific markers. Patients with high levels of cdc25B expression in tumor cells had a distant recurrence rate of 41.9% while those who expressed little or none of the cdc25B mRNA had a 29.1% recurrence rate at 10 years. Similarly, 37.2% of overexpressors versus only 19.9% of cdc25B negative patients were dead of disease at 10 years. Actuarial survival curves demonstrated that cdc25B positive patients experienced less favorable disease free survival and adjusted survival. There was a strong correlation between cdc25B overexpression and microvessel density (p=0.038), a negative prognostic feature indicative of augmented angiogenesis in breast cancer. While the relationship between cell cycle activation and angiogenesis is unclear, it is interesting to note that there was positive endothelial cell hybridization for cdc25B in microvessels in all cdc25B-positive tumors. cdc25B positivity was more frequently seen in higher histologic grade cancers (p=0.02) in which nuclear atypias are more frequent. No correlation with p53 overexpression was seen in keeping with the in vitro data showing no cooperation between cdc25 and mutation or deletion of the p53 in tumor focus formation.

Here, we have investigated a potential oncogenic function of the well known cell cycle activators, cdc25 phosphatases. In oncogenic cooperation assays it was shown that activated ras can cooperate with cdc25A or cdc25B but not with cdc25C to induce oncogenic transformation in normal primary fibroblasts. cdc25A and possibly cdc25B phosphatases were shown recently to associate with raf1 kinase, a known ras effector (Galaktionov, K., Jessus, C. and Beach, D. (1995) *Genes and Dev.,* 9:1046–1058 and U.S. Ser. No. 08/328,239). Furthermore, raf1 kinase phosphorylates and activates cdc25 phosphatases in vitro suggesting one possible mechanism for the observed synergism between ras and cdc25.

The most dramatic effect of cdc25A expression was observed in fibroblasts, specifically lacking the tumor supressor Rb1, in which introduction of the cdc25A gene alone causes oncogenic transformation. Finally, cdc25A does not cause immediate oncogenic transformation when expressed in p53–/– cells. Oncogenic mutations in ras family oncogenes occur in approximately 30% of the human cancers. Another 30% of all human cancers have mutations or deletions in Rb1 tumor supressor. The ability of cdc25 phosphatases to show oncogenic cooperation with either oncogenic ras mutants or Rb1 deletion mutants underscores the potential significance of cdc25 overexpression in the development of human malignancies.

In support of this suggestion, cdc25B was found to be highly expressed in 32% of the primary breast cancer. Tumor-specific expression of the cdc25B in human breast carcinomas correlates with less favorable prognosis and survival. Our results suggest that alterations in the function of cdc25A and cdc25B by overexpression might promote oncogenic transformation in vivo and further suggest that cdc25 phosphatases (A and B) are novel potential oncogenes.

EXAMPLE 2 cdc25 Expression Stimulated by Myc

To determine whether cdc25 genes might be transcriptionally activated in response to Myc, we used previously described cell lines that express a Myc-estradiol receptor fusion protein (MycER) (Hermeking et al. (1994) *Science* 265:2091–2093; and Wagner et al. (1994) *Genes Dev.* 8:2817–2830) that is activated by the addition of β-estradiol to the growth media (Eilers et al. (1989) *Nature* 340:66–68). We observed that activation of MycER causes activation of cdc25A gene expression. Initial induction of cdc25A was consistently detected by 3–4 hours after addition of estradiol, peaking, at approximately 8–16 hours, at a level 4–5 times higher than that at the beginning of the experiment. At the same time, a twofold induction of cdc25B was observed at the 8 hour time point. The level of the cdc25C message is quite low in both of these cell lines and did not change during estradiol treatment. Interestingly, the induction of cdc25A by β-estradiol was equal at 32° C. and 39° C. in the Val 5 cell line, which expresses a temperature sensitive p53 protein, and which undergoes apoptosis following Myc induction at 32° C. This indicates that induction of cdc25A by MycER occurs during cell cycle activation, but that expression is not affected by execution of the alternative pathway of apoptosis.

Methods

Previously described cell lines expressing MycER fusion protein (Hermeking et al. (1994) Science 265:2091–2093; and Wagner et al. (1994) Genes Dev. 8:2817–2830) were grown in DMEM (without phenol red) with 10% fetal calf serum, incubated for 48–72 hours in DMEM with 0.1% fetal calf serum and stimulated with the addition of β-estradiol to 2 μM. Cells were collected at the indicated time points and subjected to RNA extraction procedures with Trizol, as described by the manufacturer (Gibco/BRL). Approximately 10–20 μg of the total RNA from each time point were loaded on the 1% agarose gel. Northern blot analysis was performed using 1.6 kb fragment of the cdc25A, corresponding to the complete open reading frame, or 1.2 kb NotI/EcoRI fragment of the cdc25B.

EXAMPLE 3

Myc/Max Binding Sites

To investigate whether the regulation of cdc25 by c-myc might be direct, we utilized a modified precipitation assay (Okamoto et al. (1994) EMBO J. 13:4816–4822) to search for Myc/Max binding sites within genomic human cdc25A, B and C DNA clones. Briefly, genomic fragments of cdc25A, including the first exon (clone 12E, 5.6 kb), cdc25B (17K, 6.5 kb) and cdc25C (15A, 6.0 kb) were digested with Hinf I endonuclease and subjected to affinity chromatography on GST-Myc/Max complexes immobilized on glutathione sepharose. Two DNA fragments (F1 and F2) from the cdc25A genomic clone consistently bound to Myc/Max complexes. No binding was observed with sequences from the cdc25C genomic clone and a single fragment was detected in the cdc25B genomic clone. The F1 and F2 fragments mapped to the first intron of the human cdc25A gene (FIG. 1), and nucleotide sequencing revealed the presence of a single site that matched the myc consensus binding motif (MB1 and MB2, FIGS. 1 and 2). Subsequently, the genomic cdc25A clone (12E) was completely sequenced, revealing a third potential myc binding site in the second intron, MB3 (FIG. 1).

To test whether Myc/Max complexes could efficiently bind to the isolated sites, we performed electrophoretic mobility shift assays (EMSA) on each DNA fragment, confirming that they represent functional myc-binding elements in vitro. For instance, oligonucleotides, matching the Myc binding site from F1, F2 and from the second intron of the cdc25A (MB3) were also checked by EMSA. In this case, oligonucleotides corresponding to a wild type site and a single point mutant within the consensus sequence site were used to compete with the cdc25A sites. Efficient binding was observed with the Myc/Max, but not with Myc alone and was competed by the wild type, but not with the mutant binding site. Similar results were obtained for MB2 and MB3.

Methods

For the identification of the Myc/Max binding sequences within the cdc25 genomic regions we utilized an affinity chromatography procedure, similar to immunoprecipitation procedures (Okamoto et al. (1994) EMBO J. 13:4816–4822). Briefly, cdc25 (A, B and C) genomic clones were digested with the HinfI restriction endonuclease, end-labeled with $P^{32}$ and further incubated with 10 ng of the GSTC92Myc/Max complexes in the binding buffer (Ayer et al. (1993) Cell 72:211–222), followed by incubation with 20 μl of glutathione sepharose for 30 min at 4° C. Isolated complexes were washed four times in the binding buffer, eluted with proteinase K digestion, treated with phenol/chloroform and further ethanol precipitated. Precipitated material was resuspended in 10–20 μl of TE and subjected to polyacrylamide gel (PAG) electrophoresis, followed by autoradiography. Total digests were treated the same way, except affinity chromatography on the glutathione beads, and run as a control on a gel on a parallel lane with the purified material. Electrophoretic mobility shift assays (EMSA) were done either with F1 or F2 fragments or with the synthetic oligonucleotides, corresponding to MB1, MB2 or MB3 as described in the art, c.f., Ayer et al. (1993) Cell 72:211–222. Mutant oligonucleotides correspond to the same sequence as F1 and F2 with CATGTG changed to CAACTG (for A1 and A2) or CACGTG changed to CACCTG (for A3). CM-1 oligonucleotide has been described (Ayer et al. supra).

EXAMPLE 4

Transcriptional Activation

Figure 4A:
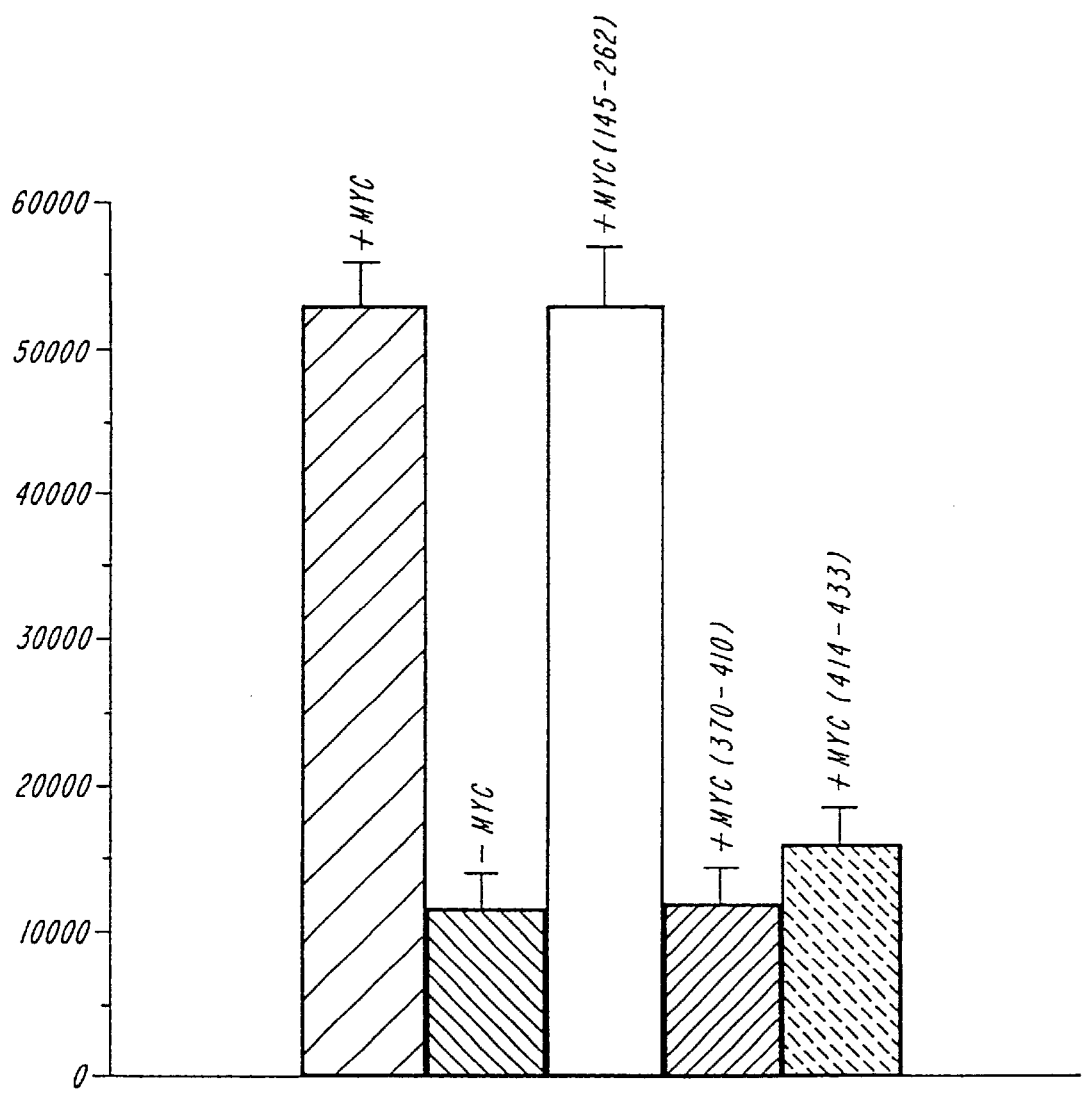
FIG. 4A is a histogram showing transcriptional activation of the luciferase reporter by c-myc.
Figure 4B:
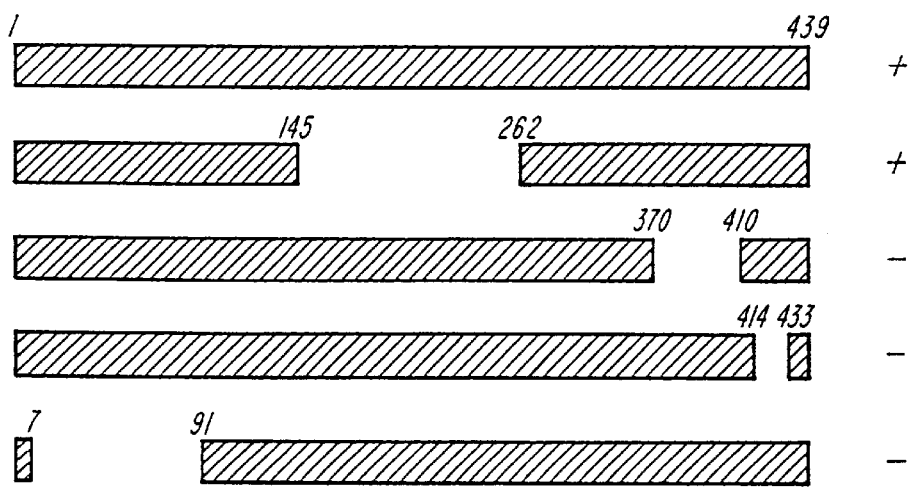
FIG. 4B is a schematic summarizing the c-myc deletion analysis regarding transcriptional activation of the luciferase reporter.

To establish whether the isolated Myc/Max binding elements might act as functional enhancers, we subcloned F1, F2, and a fragment including the third binding site, into a construct that drives luciferase gene transcription under control of the SV40 minimal promoter (pGL3 Promoter, Promega). Transient co-transfection assays, using the luciferase reporter constructs and a myc expressing plasmid pM21 (Stone et al. (1987) Mol. Cell. Biol. 7:1697–1709), were performed in 3T3 NIH cells. Introduction of a 2.5 kb cdc25A genomic fragment containing both MB2 and MB3 activated myc-driven transcription approximately fivefold (FIG. 4A). Each of the three myc binding sites individually activated myc-dependent transcription approximately 2–2.5 fold, suggesting that myc binding sites within cdc25A function synergistically. The level of activation shown here is similar to that described for other myc-binding elements, and also with the level of cdc25A induction by MycER in vivo (see example 2 above, and Gaubatz et al. (1994) Mol. Cell. Biol. 14:3853–3862). Myc mutants with deletions in the transcriptional activation (Δ7–91), helix-loop-helix (Δ371–410) and the leucine zipper domains (Δ414–433) were each inactive in transcription activation (FIG. 4B), suggesting that these domains, previously shown to be required for myc biological activity, are also important for cdc25A activation.

Methods

Cdc25A genomic fragments, containing MB2 and MB3 (2.5 kb KpnI/HindIII fragment), MB1 (F1) or MB2 (F2) were subcloned into pGL3 Promoter plasmid (Promega). These reporter plasmids were cotransfected into NIH 3T3 cells together with pM21, expressing wild type c-myc or deletion variants of c-myc (Stone et al. (1987) Mol. Cell. Biol. 7:1697–1709). Deletions in the transactivation domain (Δ7–91), internal region (Δ145–262), helix-loop-helix (Δ371–411), and leucine zipper (Δ414–433) were used. In addition, all transfections were supplemented with SV40 β-gal plasmid and carrier plasmid DNA. Luciferase and β-galactosidase assays were done as described in the art (Okamoto et al. (1994) EMBO J. 13:4816–4822). Luciferase activity was normalized against β-galactosidase activity of the same sample.

EXAMPLE 5

Cdc25A Induces Apoptosis

Physiologically relevant c-myc targets might be expected to promote two seemingly contradictory cellular responses, cell cycle activation and apoptosis. Cdc25 has long been associated with cell cycle control but not with apoptosis. To investigate whether cdc25A might trigger apoptosis, we introduced the gene, under a tetracyclin-repressible promoter, into 3T3 LI cells that have been previously shown to undergo myc-dependent DNA replication and apoptosis in growth factor depleted media (Hermeking et al. (1994) Science 265:2091–2093). We isolated two independent cell lines (hereinafter clones A10 and A12) which elevate cdc25A protein levels in response to tetracyclin removal from the media. The ectopically expressed cdc25A, fused at the N-terminus to a myc epitope tag, was detected by reduced mobility in comparison with endogenous cdc25A. Both cell lines were further studied following forced expression of cdc25A under various experimental conditions. In normal growth media, A10 cells continue to proliferate regardless of presence or absence of the cdc25A induction. Since c-myc causes apoptosis in cells that are largely depleted of growth factors, we incubated A10 cells for 48 hours in media containing 0.1% serum before removing tetracyclin. 18 hours thereafter significant cell death was observed, and at 36 hours 40–50 percent cells had died. Cell death was preceded by the morphological changes indicative of apoptosis. Control cultures incubated for the same period of time in tetracycline supplemented media showed no significant apoptosis. To ascertain, whether the observed cell death was associated with apoptosis, we performed TUNEL assays (see method description below). Upon cdc25A induction, cells displayed positive staining in parallel with morphological changes indicative of apoptosis. In addition, apoptosis in the A10 cells was associated with the development of a typical ladder of DNA degradation.

Figure 5A:
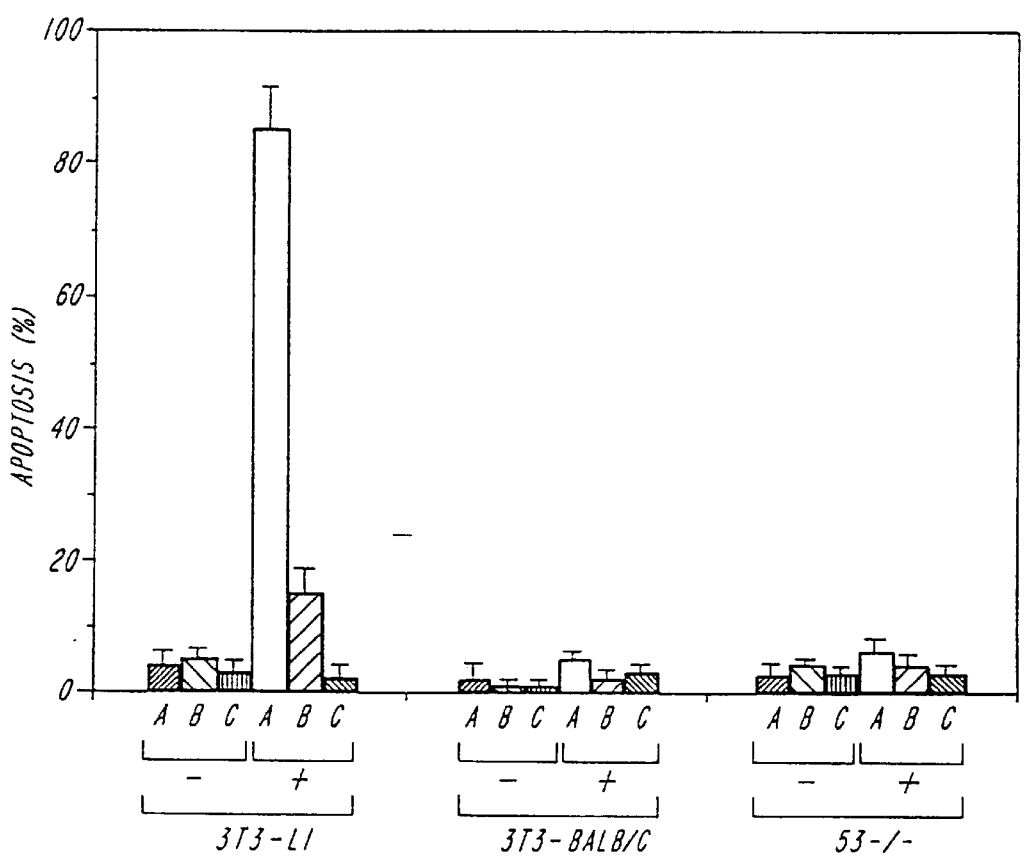
FIG. 5A illustrates induction of cell death during transient transfection with cdc25A, cdc25B, and cdc25C (a, b and c respectively).

To further explore the apoptosis caused by cdc25 expression, we introduced either cdc25A, cdc25B or cdc25C into 3T3 LI, 3T3 Balb/c and p53–/– fibroblasts in a transient transfection assays. In three independent experiments, cdc25A efficiently induced apoptosis in 3T3 LI (FIG. 5A). Cdc25B was less potent and no apoptosis was observed upon introduction of cdc25C. It has been shown previously that Myc-driven apoptosis is reduced in cells that have mutant p53. We find that, unlike 3T3 LI that carry wild type p53, 3T3 Balb/c and p53–/– fibroblasts (both lacking p53 function) support cdc25A-induced apoptosis very poorly.

Methods

Oligonucleotides, encoding 9E10 antibody-reacting epitope (myc-tag) was ligated to the NcoI cut 4g4 plasmid, containing a complete cdc25A open reading frame. Plasmid, expressing myc-tagged cdc25A (pcdc25AM) was digested with EcoRI and the resultant 2.4 kb fragment was transferred into previously described pUHD10-3 (Huibregtse et al. (1993) Mol. Cell. Biol. 13:775–784), under a tetracyclin repressible promoter, resulting in pcdc25AMtet. To generate stable cell lines with inducible cdc25A we transfected pcdc25AMtet together with the plasmid carrying Tet repressor/VP16 fusion protein, containing a neomycin resistance marker into the 3T3 LI cell line (ATCC). Stable transfectants were selected with 400 mg/ml of G418. Two colonies (out of 12 checked) were found to induce expression of cdc25A upon removal of tetracycline and were further expanded in the presence of tetracycline and G418, resulting in A10 and A12 cell lines. Expression of the myc epitope tagged cdc25A was detected by reduced mobility of the protein recognized by the anti-cdc25A antibodies or by the reaction with 9E10 antibodies. To study the effects of cdc25 overexpression in these cells, we followed previously described procedures (Hermeking et al. (1994) Science 265:2091–2093; and Wagner et al. (1994) Genes Dev. 8:2817–2830); cells were incubated for 48 hours in DMEM with 0.1% serum in the presence of 1 μg/ml tetracycline, followed by induction of cdc25A expression by changing to the media without tetracycline. Upon induction, cells were monitored and processed for TUNEL and light microscopy with fluoresceine-based ApopTag kit (Oncor). Cells were processed as described by the manufacturer, except that after fixation in 4% formalin, cells were permeabilized in 80% ethanol for 30 min at 4° C. Cells were photographed on a Zeiss Axiophote fluorescence microscope.

EXAMPLE 6

Cdc25A Role in Myc-driven Apoptosis

Figure 5B:
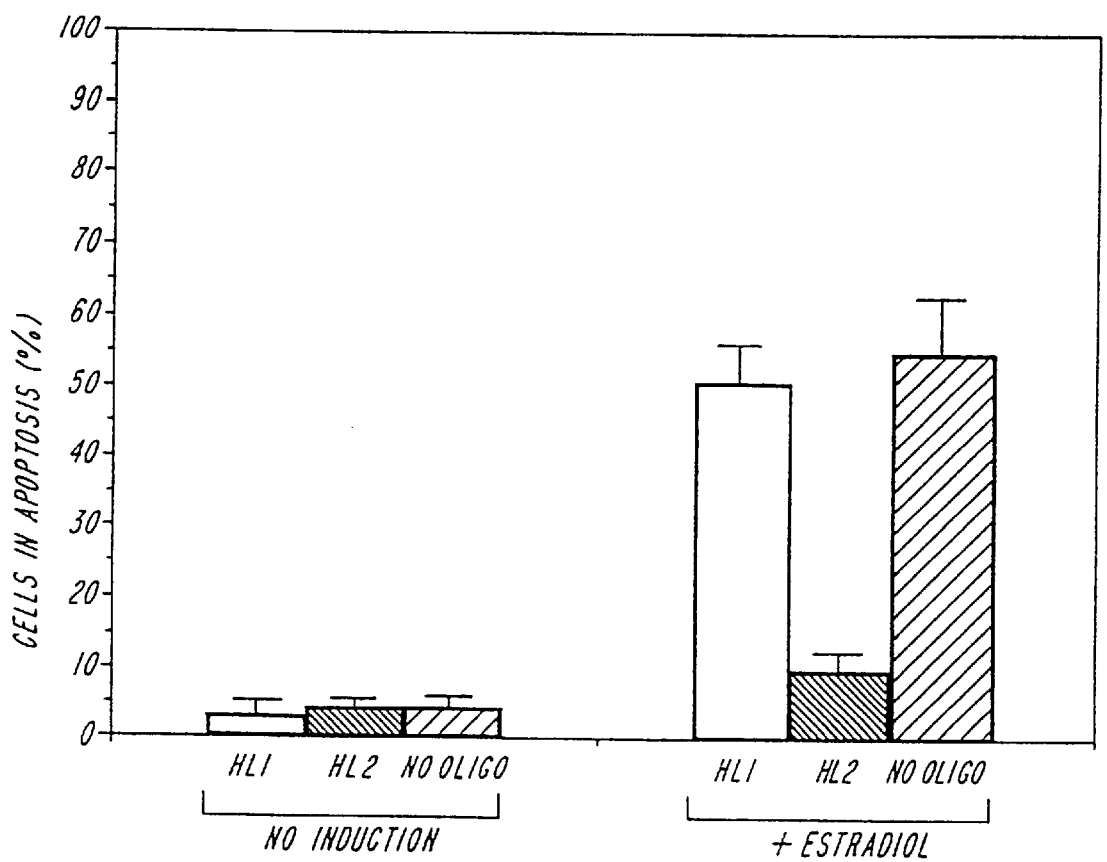
FIG. 5B illustrates inhibition of myc-induced apoptosis by antisense oligonucleotides to cdc25A.

Finally, to investigate whether induction of the cdc25A gene is essential for Myc-driven apoptosis, we incubated Val 5 cells after MycER induction by β-estradiol with an antisense cdc25A oligonucleotide. Following this incubation, cells were shifted from 39 to 32° C., activating wild type p53 function, which normally results in apoptosis (Wagner et al. (1994) Genes Dev. 8:2817–2830). A scrambled oligonucleotide with the same nucleotide content was used in control experiments. We observed that both apoptosis and DNA replocation was inhibited by the treatment with the antisense, but not with scrambled (control) oligonucleotides (FIG. 5B).

Methods

Human cdc25A, B and C under control of CMV promoter and pCMV CD20 has been described (Galaktionov et al. (1995) Science 269:1575–1577). 3T3 LI, 3T3 Balb/c and p53–/– cells were transfected as described in Galaktionov et al. supra, and 24 hours after transfection cell incubation was continued either in complete media, supplemented with 10% fetal calf serum (indicated by –) or in growth media with 0.1% serum (indicated by +). Apoptotic figures were scored 24 hours later upon microscopic investigation of the cultures based on CD20 staining, indicative of successful transfection (more than 2%, usually 8–10%), and visible morphological changes indicative of cell death (membrane blebbing, chromatin condensation, etc.). In another embodiment, Val 10 cells were grown in DMEM (without phenol red) in 10% fetal calf serum at 39° C., shifted to 0.1% serum content at 32° C. for 24 hours, incubated for another 24 hours with cdc25A antisense 20-mer S-oligonucleotide (obtained from Oligo Etc.), spanning the initiation methionine region (GCTCGGGCCCAGTTCCATGG) of both human and mouse cdc25A or scrambled oligonucleotide (GGTACCTTGACCCGGGCTCG) as control. 48 hours after shifting to 0.1% serum, MycER fusion protein was induced by the addition of β-estradiol and cell incubation continued for another 24 hours, at which point cells were photographed and apoptosis was scored by TUNEL.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A recombinant cell comprising (i) a recombinant cdc25 phosphatase gene, and (ii) a reporter gene under transcriptional control of a p53-responsive element, wherein a level of expression of the reporter gene is indicative of a level of activity of the cdc25 phosphatase.

2. The recombinant cell of claim 1, wherein the recombinant cdc25 gene comprises a transcriptional regulatory sequence providing for inducible expression of a cdc25 phosphatase encoded by said gene.

3. The recombinant cell of claim 2, wherein the recombinant cdc25 gene encodes a mammalian cdc25 phosphatase.

4. The recombinant cell of claim 3, wherein the mammalian cdc25 phosphatase is a human cdc25 phosphatase.

5. The recombinant cell of claim 4, wherein the human cdc25 phosphatase is selected from the group consisting of cdc25A, cdc25B and cdc25C.

6. The recombinant cell of claim 1, which cell is a mammalian cell.

7. The recombinant cell of claim 6, which cell is a human cell.

8. The recombinant cell of claim 1, which cell comprises at least one functional p53 tumor suppressor allele.

* * * * *

UNITED STATES PATENT AND TRADEMARK OFFICE
CERTIFICATE OF CORRECTION

PATENT NO.    : 6,322,975 B1
DATED         : November 27, 2001
INVENTOR(S)   : David H. Beach and Konstantin Galaktionov It is certified that error appears in the above-identified patent and that said Letters Patent is hereby corrected as shown below:

Column 1,
Line 6, insert:
-- GOVERNMENT SUPPORT
The invention was partially funded by NIH Grant No. RO1 GM39620. The Government has certain rights to the invention. --

Column 33,
Line 11, replace "claim 2" with -- claim 1 --.

Signed and Sealed this

Twenty-eighth Day of May, 2002

*Attest:*

JAMES E. ROGAN
*Attesting Officer*      *Director of the United States Patent and Trademark Office*

UNITED STATES PATENT AND TRADEMARK OFFICE
CERTIFICATE OF CORRECTION

PATENT NO. : 6,322,975 B1
DATED : November 27, 2001
INVENTOR(S) : Beach et al.

It is certified that error appears in the above-identified patent and that said Letters Patent is hereby corrected as shown below:

<u>Title page,</u>
Item [73], Assignees, immediately following Item [76], Inventors add:
-- [73] Assignees: Cold Spring Harbor Laboratory (Cold Spring Harbor, NY) --

Signed and Sealed this

Ninth Day of September, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAGTCGTGTT TGTGTTTGAC CCGCGGGCGC CGGTGGCGGC GGCCGAGGCC GGTGTCGGCG    60

GGGCGGGGCG GTCGCGGCGG AGGCAGAGGA AGAGGGAGCG GGAGCTCTGC GAGGCCGGGC   120

GCCGCCATGG AACTAGGCCC GGAGCCCCCG CACCGCCGCC GCCTGCTCTT CGCCTGCAGC   180

CCCCCTCCCG CGTCGCAGCC CGTCGTGAAG GCGCTATTTG GCGCTTCAGC CGCCGGGGGA   240

CTGTCGCCTG TCACCAACCT GACCGTCACT ATGGACCAGC TGCAGGGTCT TGGCAGGTAA   300

GGAGAGACCG CGGGCGGTGC TCCGGGCCCC TGGCCTCGGT GTCGGCCTTG GAGAGTTCAG   360

GCCAGGAAAC GGACCGGGAG AAGGGCGAGA CCCGTCCGTC CGGGTTCGCC GCTCGGGGAC   420

AGCCGGGCTA GGGCCTGCCA TGTGCACCCC GCCCGGGCGG AATGTTGGCC GGGAGAGGCC   480

GTCGGGACTT CCAGGGGAAG AGGTGGAGAT CCTTGGGCCT AAGCCCGACC AGGCCCCCC    539
```

(2) INFORMATION FOR SEQ ID NO:2:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
GAGTCGGGAT GAAAGTTGAA CAGGACACTT TCTGCTTTTC AGAAGTTGGG AAACGCACAA    60

GACATGTGCT TAGCAAACGG GATGCCAGAG ATTGAAGGGA AAGTAGCTCT TCCGCGGGAA   120

ACACCGTGGG ATGCATTTTT TGCTATCAGG AAAAGCCCAG GAAGCTTTCT GAAAGTTGGG   180

TAAAAAGACC TGGCCTTAGG AAAGCAGCAG AGTGGACATC AGGAATGTGC ACAGGGCGAG   240

GGACTGAGAT GATTTTACAT AAACGCCAGG AAAGGAAATG CCATGGTCCT TTGTTGAGAA   300

GGAACAAAGA TCACAGCAAA CGAAGATCCT GAGGATGGTT TAGAAAAGGG TGAAAGTGAG   360

TGCCTAGAAG AGCCTGATTT TCCCGCGGGG GTAGATT                             397
```

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGCCTGCCA TGTGCACCCC GCCCGGG                                         27
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCACAAGACA TGTGCTTAGC AAACGGG                                     27

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ACTACAGACA CGTGCCACCA CACCCAA                                     27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TGTGCGGCCA CGTGTCGCGA GGCCCCG                                     27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCAGGGGACA CGTGGTCGCC GAGCGNN                                     27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCAACGAGCA CGTGGCCTGG GGCGCCA                                     27